US010821172B2

United States Patent
Tian et al.

(10) Patent No.: US 10,821,172 B2
(45) Date of Patent: Nov. 3, 2020

(54) VACCINE COMPOSITION AND PREPARATION METHOD AND USE THEREOF

(71) Applicant: PULIKE BIOLOGICAL ENGINEERING, INC., Luoyang (CN)

(72) Inventors: Kegong Tian, Luoyang (CN); Yi Cheng, Luoyang (CN); Wenqiang Pang, Luoyang (CN); Jinzhong Sun, Luoyang (CN); Xuke Zhang, Luoyang (CN)

(73) Assignee: PULIKE BIOLOGICAL ENGINEERING, INC., Luoyang (CN)

( * ) Notice: Subject to any disclaimer, the term of this patent is extended or adjusted under 35 U.S.C. 154(b) by 167 days.

(21) Appl. No.: 16/074,724

(22) PCT Filed: Nov. 3, 2017

(86) PCT No.: PCT/CN2017/109358
§ 371 (c)(1),
(2) Date: Aug. 1, 2018

(87) PCT Pub. No.: WO2018/176837
PCT Pub. Date: Oct. 4, 2018

(65) Prior Publication Data
US 2018/0353595 A1  Dec. 13, 2018

(30) Foreign Application Priority Data
Apr. 1, 2017 (CN) .......................... 2017 1 0213661

(51) Int. Cl.
*A61K 39/235* (2006.01)
*A61K 39/17* (2006.01)
*A61K 39/145* (2006.01)
*A61K 39/215* (2006.01)
*A61P 31/20* (2006.01)
*A61K 39/12* (2006.01)
*A61K 39/00* (2006.01)

(52) U.S. Cl.
CPC ............ *A61K 39/235* (2013.01); *A61K 39/12* (2013.01); *A61K 39/145* (2013.01); *A61K 39/17* (2013.01); *A61K 39/215* (2013.01); *A61P 31/20* (2018.01); *A61K 2039/5252* (2013.01); *A61K 2039/552* (2013.01); *A61K 2039/55566* (2013.01); *A61K 2039/70* (2013.01); *C12N 2710/10034* (2013.01); *C12N 2720/10034* (2013.01); *C12N 2760/16034* (2013.01); *C12N 2760/18134* (2013.01); *C12N 2770/20034* (2013.01)

(58) Field of Classification Search
None
See application file for complete search history.

(56) References Cited

U.S. PATENT DOCUMENTS

| | | | | |
|---|---|---|---|---|
| 5,750,113 A | * | 5/1998 | Cook | A61K 39/215 424/184.1 |
| 2005/0266019 A1 | * | 12/2005 | Rodenberg | A61K 39/12 424/199.1 |
| 2009/0081255 A1 | * | 3/2009 | Bublot | A61K 39/12 424/210.1 |
| 2017/0232096 A1 | * | 8/2017 | Lozano-Dubernard | A61K 39/145 424/199.1 |
| 2018/0353595 A1 | * | 12/2018 | Tian | A61P 31/20 |

FOREIGN PATENT DOCUMENTS

| | | |
|---|---|---|
| CN | 101955950 A | 1/2011 |
| CN | 106232813 A | 12/2016 |
| WO | WO 2015/024932 * | 2/2015 |
| WO | WO 2016/020885 * | 2/2016 |

OTHER PUBLICATIONS

Sequence alignment of SEQ ID No. 2 with GenEmbl db access No. EF625961 by Cui et al 2007.*
Cheng et al. (Journal of Vaccines and Immunology. Oct. 2016; 2 (1): 019-022).*
Fingerut et al. (Vaccine. 2003; 21; 2761-2766).*
Li etal. "Comparison of ND-AL Recombined Vaccine and ND-IB-EDS Triple Vaccine Using Different Types of Adjuvant." China Poultry 8 (2010): 008).*
Jin et al. (Derwent abstract of CN101607083; Dec. 2003).*
International Search Report for PCT Application No. PCT/CN2017/109358, dated Feb. 2, 2018, 13 pages.
Spackman, "Methods in Molecular Biology™", vol. 436, Avian influenza virus, 2008, 147 pages.
Lidgate, "Preparation of the Syntex Adjuvant Formulation (SAF, SAF-m, SAF-1)", Methods in Molecular Medicine, vol. 42: Vaccine Adjuvants: Preparation Methods and Research Protocols, Springer Protocols—Jan. 1, 2000, pp. 229-237.

* cited by examiner

*Primary Examiner* — Shanon A. Foley
(74) *Attorney, Agent, or Firm* — Ditthavong & Steiner, P.C.

(57) ABSTRACT

The present disclosure provides a vaccine composition comprising an immune amount of Fiber protein of egg drop syndrome virus or an immune amount of a live vector recombined with gene of the Fiber protein of egg drop syndrome virus and a veterinarily acceptable carrier.

17 Claims, No Drawings
Specification includes a Sequence Listing.

VACCINE COMPOSITION AND PREPARATION METHOD AND USE THEREOF

CROSS-REFERENCES TO RELATED APPLICATIONS

This application claims priority from PCT Application Serial No. PCT/CN2017/109358, entitled "Vaccine Composition and Preparation Method and Use Thereof," filed on Nov. 3, 2017, which claims priority from a Chinese Application Serial No. 201710213661.6, filed on Apr. 1, 2017, the contents of which are hereby incorporated herein in their entirety by this reference.

FIELD OF TECHNOLOGY

The present disclosure relates to a vaccine composition against avian egg drop syndrome virus and a preparation method and use thereof, belonging to the field of biomedicine.

BACKGROUND ART

Egg drop syndrome virus (EDSV) belongs to the group III of avian adenovirus. Poultry infected with this virus has no obvious clinical symptom, some of which may have slight diarrhea. The infection occurs frequently during a peak of egg laying, resulting in soft eggshells, thin eggshells, shell-less eggs and a serious decline in egg production rate, and causing serious economic losses.

EDSV has a typical morphology of adenovirus, without any envelope and with hemagglutination activity, which proliferates in the fallopian tubes of poultry. The genome of the EDSV is a linear double-stranded DNA of about 33 kb. The viral particles consist of structural proteins, the nucleocapsid has a diameter of 70 to 80 nm. The EDSV is icosahedrally symmetrical with DNA encapsidated in the capsid. The nucleocapsid consists of 252 capsid particles, of which 240 are Hexon proteins, forming 20 faces and most edges of an icosahedron. These capsid particles are prismatic, 7 nm wide and 11 nm long. The other 12 are pentons (Penton proteins), located at 12 vertices of the icosahedron. Each Penton protein has a fiber protrusion (Fiber protein).

The egg drop syndrome is currently one of the most crucial diseases that seriously endanger the development of poultry industry in the world. Among various prevention and control measures, vaccination is still the most vital measure. The current EDS inactivated vaccine commonly used in the poultry industry is a vaccine obtained through emulsification of viruses amplified in duck embryos with a mineral oil adjuvant after inactivation. However, since it is difficult to obtain a high titer of virus from cultivation of EDSV in duck embryos, it is often difficult to provide a desired immune effect with prepared vaccine. In addition, the way of production of the virus antigen is completely dependent on the duck embryos. Once influenza and other infectious diseases occur, supply of duck hatching eggs could be insufficient which would seriously affect prevention and control of egg drop syndrome. In addition, there is a risk of biosafety caused by incomplete inactivation of viruses during production of whole-virus vaccine.

Subunit vaccine is a new reliable type of genetically engineered vaccine developed in recent years. Hexon (240/252) is a main object in the study of subunit vaccine of egg drop syndrome virus. However, the immunological efficiency of its subunit vaccine has been low, and the subunit vaccine has not been developed into products. No protein used for vaccines with good immunogenicity has been prepared in the prior art. So far no subunit vaccine of EDSV has appeared on the market. Therefore, it is urgently necessary to develop a subunit vaccine composition with good immunological effect, which can effectively prevent the spread of the disease and can be free from the influence of fluctuation of duck egg supply.

DESCRIPTION

In order to solve the deficiency of the prior art, the disclosure provides an immunogenic protein of egg drop syndrome virus, a vaccine composition prepared therefrom and a preparation method and use of the vaccine composition; the vaccine composition can effectively prevent and/or treat infection of the egg drop syndrome virus.

The disclosure relates to a vaccine composition against egg drop syndrome virus, wherein the vaccine composition comprises an immune amount of antigen of egg drop syndrome virus and a veterinarily acceptable carrier; wherein the antigen of egg drop syndrome virus comprises a subunit antigen of immunogenic protein of the egg drop syndrome virus as described in the present disclosure or a live vector recombined with gene of the immunogenic protein of the egg drop syndrome virus.

The disclosure relates to a vaccine composition against egg drop syndrome virus, wherein the vaccine composition comprises an immune amount of antigen of egg drop syndrome virus and a veterinarily acceptable carrier; wherein, the antigen of egg drop syndrome virus is an antigen of Fiber protein of egg drop syndrome virus or a live vector recombined with gene of the Fiber protein of egg drop syndrome virus.

The disclosure also relates to a preparation method of the vaccine composition, the preparation method comprises the following steps of: (1) cloning a gene of the egg drop syndrome virus protein; (2) transforming and recombining the gene of the egg drop syndrome virus protein cloned in the step (1); (3) expressing the recombinant egg drop syndrome virus protein; (4) isolating and purifying the recombinant egg drop syndrome virus protein, and treating the purified recombinant egg drop syndrome virus protein with a non-ionic surfactant; and (5) mixing the egg drop syndrome virus protein with an adjuvant based on a certain ratio and emulsifying the resulting mixture.

The disclosure also relates to a use of the vaccine composition according to the disclosure in preparing medicine for treatment and prevention of diseases related to infection of egg drop syndrome virus.

The present disclosure is the first to prepare the vaccine composition by adopting the EDSV Fiber protein after bulk expression of the gene of selected EDSV protein. The vaccine composition prepared by the EDSV Fiber protein can prevent and/or treat an outbreak of the egg drop syndrome virus, and the body of the animal after being immunized with the vaccine composition containing the protein can rapidly produce antibody. The vaccine composition has good prevention and control effect on infection of EDSV alone or in combination with other viruses, with good biosecurity.

The vaccine composition prepared by the EDSV Fiber protein can provide complete protection to the chickens and ducks with good immunogenicity and effectively prevent wild-type strains from a variety of geographical origins, and can be used for preventing and/or treating the infection of EDSV in clinical practice.

DETAILED DESCRIPTION

Hereinafter, embodiments of the present disclosure will be described.

The term "Egg Drop Syndrome Virus" (EDSV) belongs to group III of avian adenovirus and the genome is double-stranded DNA. The resulting clinical symptoms include production of soft eggshells, thin eggshells, and shell-less eggs, and a serious decline in egg production rate. Pathological changes are characterized by ovarian quiescence and tubal atrophy.

The disclosure relates to a vaccine composition against egg drop syndrome virus, wherein the vaccine composition comprises an immune amount of antigen of egg drop syndrome virus and a veterinarily acceptable carrier; the antigen of egg drop syndrome virus is an antigen of Fiber protein of egg drop syndrome virus or a live vector recombined with gene of the Fiber protein of egg drop syndrome virus.

For the first time, the present disclosure has found that Fiber protein, which is present in a very little amount on the surface of capsid particles of egg drop syndrome virus, has good immunogenicity, either the subunit antigen prepared therefrom or the live vector recombined with its gene can produce good immunological efficacy after immunization and provide a protection rate of 100% to chickens and ducks.

The term "vaccine composition" as used in the present disclosure refers to a pharmaceutical composition having immunogenicity of egg drop syndrome virus, which can induce, stimulate or enhance the immune response of chickens and ducks to the egg drop syndrome virus.

The term "immune amount" should be understood as an "immunologically effective amount," also refers to an immunoprotective amount or an effective amount to produce an immune response, which is an amount of antigen effective to induce an immune response in a body of a recipient, which immune amount is sufficient to prevent or ameliorate signs or symptoms of a disease including adverse health effects or complications of the disease. The immune response may be sufficient for diagnostic purposes or other tests or may be suitable for use in preventing signs or symptoms of a disease, including adverse health consequences caused by an infection caused by a pathogen, or complications of the disease. Humoral immunity or cell-mediated immunity or both may be induced. The immune response of the animal to the immunogenic composition may be assessed indirectly, for example, by measuring antibody titers and analyzing lymphocyte proliferation, or directly by monitoring signs or symptoms after challenge with wild-type strains, while protective immunity provided by the vaccine may be assessed by measuring, for example, clinical signs of subjects such as mortality, reduction in morbidity, temperature values, and overall physiological condition and overall health and performance of the subjects. The immune response may include, but is not limited to induction of cellular and/or humoral immunity.

The term "antigen of egg drop syndrome virus" refers to any composition that contains at least one form of antigen of egg drop syndrome virus which can induce, stimulate or enhance an immune response against infection of egg drop syndrome virus, the forms of the antigen include but are not limited to inactivated, attenuated or subunit antigens.

The Fiber protein antigen of egg drop syndrome virus of the disclosure may be prepared by recombined and expressed subunit antigen of the Fiber protein, of which the expression system used may be eukaryotic expression systems or prokaryotic expression systems, or alternatively, the Fiber protein antigen of egg drop syndrome virus may be synthetic peptide antigen artificially synthesized.

The "subunit antigen" refers to an antigen that is prepared by genetically engineering a protective antigen gene of a pathogen into a prokaryotic or eukaryotic expression system for efficient expression. It is less likely to cause side effects compared to the whole-virus antigens.

The "synthetic peptide antigen" refers to a small peptide that contains only a component of an immunological determinant, that is, an antigen that is prepared by synthesizing a protective short peptide according to the amino acid sequence of a natural protein by an artificial method, linking this protective short peptide with a vector, and adding an adjuvant.

The "live vectors" refers to non-pathogenic microorganisms which carry and express a gene of an antigenic or antigenic determinant by mean of genetic engineering as to produce immunogenicity. The non-pathogenic microorganisms may be bacteria and viruses, viruses that are often used as viral live vectors include vaccinia virus, fowlpox virus, turkey herpes virus, adenovirus, pseudorabies virus, retrovirus, lentivirus; bacterial live vectors may include attenuated *Salmonella*, BCG, attenuated *Listeria monocytogenes*, attenuated *Vibrio cholerae*, attenuated *Shigella*, *Lactococcus lactis*, *Lactobacillus plantarum*, and *Streptococcus gordonii*.

As an embodiment of the present disclosure, the Fiber protein of egg drop syndrome virus in the vaccine composition of the present disclosure is a protein encoded by a nucleotide sequence shown in SEQ ID NO. 1.

As an embodiment of the present disclosure, the Fiber protein of egg drop syndrome virus in the vaccine composition of the present disclosure is a protein encoded by a nucleotide sequence shown in SEQ ID NO. 2.

As an embodiment of the present disclosure, the gene that encodes the Fiber protein of egg drop syndrome virus in the vaccine composition of the present disclosure has a nucleotide sequence shown in SEQ ID NO. 1 or a degenerate sequence thereof.

As an embodiment of the present disclosure, the gene that encodes the Fiber protein of egg drop syndrome virus in the vaccine composition of the present disclosure has a nucleotide sequence shown in SEQ ID NO. 2 or a degenerate sequence thereof.

As an embodiment of the present disclosure, the HA titer of the antigen of the Fiber protein of egg drop syndrome virus in the vaccine composition of the present disclosure is equal to or greater than 1:32.

As a preferred embodiment of the present disclosure, the HA titer of the antigen of the Fiber protein of egg drop syndrome virus in the vaccine composition of the present disclosure is within a range of 1:32-1:128.

As a more preferred embodiment of the present disclosure, the HA titer of the antigen of the Fiber protein of egg drop syndrome virus in the vaccine composition of the present disclosure is within a range of 1:32-1:64.

The HA titer of the antigen of the Fiber protein of egg drop syndrome virus in the vaccine composition of the present disclosure may also be within a range of 1:64-1:128.

As an embodiment of the present disclosure, the live vector of the Fiber protein gene of egg drop syndrome virus in the vaccine composition of the present disclosure is recombinant attenuated *Salmonella*, recombinant Newcastle disease virus or recombinant poxvirus.

Because the live vector vaccine composition of the present disclosure combines the advantages of an inactivated vaccine and a live vaccine, it can ensure that the laying fowls can be protected in terms of the immunological efficacy, and immunological efficacy of the live vector vaccine composition is so strong that adjuvants may not be added.

The term "veterinarily acceptable carrier" refers to all components other than the antigen of egg drop syndrome virus in the vaccine composition of the present disclosure which are carriers or diluents that do not cause significant irritation to an organism and do not abrogate the biological activity and properties of the administered compounds, preferably an adjuvant.

The vaccine composition of the disclosure may further be added with other reagents.

As an embodiment of the present disclosure, the veterinarily acceptable carrier includes drugs, immunostimulants, antioxidants, surfactants, colorants, volatile oils, buffers, dispersants, propellants and preservatives; the immunostimulants include α-interferon, β-interferon, γ-interferon, granulocyte-macrophage colony stimulating factor (GM-CSF), macrophage colony stimulating factor (M-CSF) and interleukin 2 (IL2).

Preferably, the immunostimulants comprise α-interferon, β-interferon, γ-interferon, granulocyte-macrophage colony stimulating factor (GM-CSF), macrophage colony stimulating factor (M-CSF) and interleukin 2 (IL2).

Methods well known in the art can be used to prepare such compositions.

The term "adjuvant" may includes a compound selected from a group consisting of alhydrogel adjuvant, saponins e.g., Quil A. QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion, the polymers of acrylic or methaciylic acid and the copolymers of maleic anhydride and alkenyl derivative. The term "emulsion" may be based in particular on light liquid paraffin oil (European Pharmacopea type); isoprenoid oil, such as squalane or squalene oil, resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol. of propylene glycol and of oleic, isostearic, ricinoleic or hydroxy-stearic acid, which are optionally ethoxylated, and polyoxypropylene-polyoxyethylene block copolymers, in particular the Pluronic products, especially L121. See Hunter et al., The Theory and Practical Application of Adjuvants (Ed. Stewart-Tull, D. E. S). John Wiley and Sons, NY, pp 51-94 (1995) and Todd et al. Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of the same book. The term "polymers of acrylic or methacrylic acid" preferably are the polymers of acrylic or methacrylic acid which are cross-linked, especially with polyalkenyl ethers of sugars or polyalcohols. These compounds are known by the term carbomer (Trade name, Carbopol) (Phameuropa Vol. 8, No. 2, June 1996). Persons skilled in the art can also refer to U.S. Pat. No. 2,909,462 which describes such acrylic polymers cross-linked with a polyhydroxylated compounds having at least 3 hydroxyl groups, preferably not more than 8, the hydrogen atoms of at least three hydroxyls being replaced by unsaturated aliphatic radicals having at least 2 carbon atoms. The preferred radicals are those containing 2 to 4 carbon atoms, e.g. vinyls, allyls and other ethylenically unsaturated groups. The unsaturated radicals themselves may contain other substituents, such as the methyl group. The products sold under the name CARBOPOL® (BF Goodrich, Ohio. USA) are particularly appropriate. They are cross-linked with allyl sucrose or with allyl pentaerythritol. Among them, there may be mentioned Carbopol 974P, 934P and 971 P, most preferably Carbopol 971P. For the term "copolymerrs of maleic anhydride and alkenyl derivative", EMA (Monsanto), which is the copolymer of maleic anhydride and ethylene, can also be considered. The dissolution of these polymers in water leads to an acid solution that will be neutralized, preferably to physiological pH, in order to give the adjuvant solution, into which the immunogenic, immunological or vaccine composition itself will be incorporated. The term "adjuvant" includes, but is not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, muramyl dipeptide, and Gel adjuvant among many others. Preferably, the adjuvant includes one or more of alhydrogel adjuvant, saponins, water-in-oil emulsion, oil-in-water emulsion, water-in-oil-in-water emulsion, the polymers of acrylic or methaciylic acid, the copolymers of maleic anhydride and alkenyl derivative, the RIBI adjuvant system, Block co-polymer, SAF-M, monophosphoryl lipid A, Avridine lipid-amine adjuvant, heat-labile enterotoxin from *E. coli*, cholera toxin, IMS 1314, muramyl dipeptide and Gel adjuvant.

As an embodiment of the present disclosure, the pharmaceutically acceptable carrier includes an adjuvant, which includes one or more of (1) alhydrogel adjuvant, saponins, Avridine, DDA; (2) water-in-oil emulsion, oil-in-water emulsion, water-in-oil-in-water emulsion; or (3) the polymers of acrylic or methaciylic acid, the copolymers of maleic anhydride and alkenyl derivative; and the RIBI adjuvant system, Block co-polymer, SAF-M, monophosphoryl lipid A, lipid-amine adjuvant, heat-labile enterotoxin from *E. coli*, cholera toxin, IMS 1314, muramyl dipeptide and Gel adjuvant.

Preferably, the saponin is Quil A, QS-21 or GPI-0100;

Preferably, the emulsions are SPT emulsion and MF59 emulsion, or the emulsions are formed by combination of oil and emulsifiers, the emulsions can be based in particular on light liquid paraffin oil; isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters; the emulsifiers are nonionic surfactants, in particular esters of Polyoxyethylene fatty acid (e.g. oleic acid), of sorbitan, of mannide (e.g. anhydromannitol oleate), of glycol, of polyglycerol, of propylene glycol and of oleic, isostearic, ricinoleic or hydroxy-stearic acid, which are optionally ethoxylated, ethers of fatty alcohols and polyhydric alcohols (e.g. oleyl alcohol) and polyoxypropylene-polyoxyethylene block copolymers, in particular the Pluronic®, especially L121;

Preferably, the polymers of acrylic or methacrylic acid are compounds known by carbomer, in which the polymers of acrylic or methacrylic acid are cross-linked, especially with polyalkenyl ethers of sugars or polyalcohols, preferably, Carbopol 974P, 934P or 971P.

Preferably, the copolymerrs of maleic anhydride and alkenyl derivative are copolymers EMA of maleic anhydride and ethylene.

Preferably, the adjuvant is a white oil adjuvant for preparation of water-in-oil emulsion.

The concentration of the adjuvant ranges from 5% to 70% V/V, preferably from 30% to 70% V/V, more preferably 66% V/V. The Fiber protein gene of the egg drop syndrome virus according to the present disclosure can also be applied to the development of expression vectors, nucleic acid vaccines, diagnostic reagents, and other drugs for preventing and/or treating the egg drop syndrome.

The present disclosure relates to a recombinant vector capable of expressing the Fiber protein encoded by the nucleotide sequence according to the present disclosure which is immunogenic and capable of producing an immune response.

The present disclosure relates to a transformant containing an introduced recombinant vector expressing the Fiber protein according to the present disclosure.

The Fiber protein of the disclosure may be prepared by any method known in the art, for example by recombinant expression of the Fiber protein gene, the expression system used may be any known expression system, for example: eukaryotic expression systems, or prokaryotic expression systems. Alternatively, the Fiber protein sequence may be synthesized directly. The eukaryotic expression systems can include mammalian cell expression systems, yeast expression systems, and insect expression systems.

The vaccine composition according to the present disclosure further comprises a combination of other pathogens or antigens to prepare a combined vaccine or a complex vaccine against infection of various diseases including egg drop syndrome virus.

The term "combined vaccine" refers to a vaccine prepared with the virus mixture by mixing the FADV in the present disclosure with at least one other different virus. The term "complex vaccine" refers to a vaccine prepared from FADV and bacterium. For example, the FADV in the present disclosure may be mixed or combined with Newcastle disease virus, avian infectious bronchitis virus, avian influenza virus, infectious bursal disease virus, fowl adenovirus, avian reovirus and/or *Escherichia coli, avibacterium paragallinarum, Mycoplasma synoviae* and *Mycoplasma gallisepticum*.

As an embodiment of the present disclosure, the vaccine composition further comprises one or more of the following antigens including an antigen of Newcastle disease virus, an antigen of avian influenza virus, an antigen of avian infectious bronchitis virus, an antigen of infectious bursal disease, an antigen of fowl adenovirus, an antigen of avian reovirus, an antigen of *Escherichia coli*, an antigen of *avibacterium paragallinarum*, an antigen of *Mycoplasma Synoviae*, an antigen of *Mycoplasma gallisepticum*, an antigen of *Pasteurella multocida*, an antigen of Marek's disease virus, an antigen of avian encephalomyelitis virus and an antigen of infectious laryngotracheitis virus.

As a preferred embodiment of the present disclosure, the vaccine composition further comprises one or more of the following antigens including an inactivated antigen of Newcastle disease virus, an inactivated antigen of avian influenza virus, an inactivated antigen of avian infectious bronchitis virus, a subunit antigen of infectious bursal disease virus, and an inactivated antigen or a subunit antigen of fowl adenovirus.

As a preferred embodiment of the present disclosure, the inactivated antigen of Newcastle disease virus is an inactivated antigen of N7a strain, the inactivated antigen of avian influenza virus are inactivated antigens of SZ strain, the inactivated antigen of avian infectious bronchitis virus are inactivated antigen of M41 strain, the subunit antigen of infectious bursal disease virus are VP2 protein of infectious bursal disease virus, the inactivated antigen of fowl adenovirus are inactivated antigens of FAV-HN strain, and the subunit antigen of fowl adenovirus are Penton protein or Fiber-2 protein of the fowl adenovirus.

As an embodiment of the present disclosure, the HA titer of the Fiber protein of the egg drop syndrome virus is between 1:32 and 1:128, the content of the inactivated antigen of the Newcastle disease virus is $10^{8.0}$-$10^{9.0}$ $EID_{50}$/0.1 ml before inactivation, the content of the inactivated antigen of the avian influenza virus is $10^{6.5}$-$10^{8.5}$ $EID_{50}$/0.1 ml before inactivation, the content of the inactivated antigen of the avian infectious bronchitis virus is $10^{6.0}$-$10^{7.0}$ $EID_{50}$/0.1 ml before inactivation, and the AGP titer of the VP2 protein of the avian infectious bursal disease virus is between 1:16 and 1:128, the AGP titer of the Penton protein of the fowl adenovirus is between 1:2 and 1:16, and the AGP titer of the Fiber-2 protein of the fowl adenovirus is between 1:2 and 1:16.

As an embodiment of the present disclosure, the HA titer of the Fiber protein of the egg drop syndrome virus is between 1:32 and 1:128, the content of the inactivated antigen of the Newcastle disease virus is $10^{8.0}$ $EID_{50}$/0.1 ml before inactivation, the content of the inactivated antigen of the avian influenza virus is $10^{8.0}$ $EID_{50}$/0.1 ml before inactivation, the content of the inactivated antigen of the avian infectious bronchitis virus is $10^{6.0}$ $EID_{50}$/0.1 ml before inactivation, and the AGP titer of the VP2 protein of the avian infectious bursal disease virus is 1:16, the AGP titer of the Penton protein of the fowl adenovirus is 1:4, and the AGP titer of the Fiber-2 protein of the fowl adenovirus is 1:4.

The present disclosure also relates to a method for preparing said vaccine composition, wherein said method comprises: step (1), cloning a gene of the Fiber protein of the egg drop syndrome virus and recombining the gene of the Fiber protein of the egg drop syndrome virus into an expression vector so as to obtain a recombinant expression vector recombined with the gene of the Fiber protein of the egg drop syndrome virus; step (2), transforming the recombinant expression vector recombined with the gene of the Fiber protein of the egg drop syndrome virus and an expression vector of a molecular chaperone into *Escherichia coli* in order to express the Fiber protein of the egg drop syndrome virus; step (3), treating the expressed the Fiber protein of the egg drop syndrome virus with a non-ionic surfactant in order to remove endotoxin; and step (4), mixing the Fiber protein of the egg drop syndrome virus in which the endotoxin is removed with an adjuvant to obtain the vaccine composition.

As an embodiment of the present disclosure, in the method for preparing the vaccine composition, the recombinant expression vector recombined with the gene of the Fiber protein of the egg drop syndrome virus in the step (1) is a recombinant pET28a Plasmid, the expression vector of the molecular chaperone in the step (2) is pG-Tf2, the Escherichia coli in the step (2) is Escherichia coli BL21 (DE3); the nonionic surfactant in the step (3) is Triton X-114.

The disclosure also relates to a use of the vaccine composition according to the disclosure in preparing medicine for treatment and/or prevention of egg drop syndrome.

The disclosure also relates to a use of the vaccine composition according to the disclosure in preparing medicine for treatment and/or prevention of infection of egg drop syndrome virus.

Subjects that may be administered with the medicine for treatment and/or prevention of infection of egg drop syndrome virus according to the present disclosure include chickens or ducks.

The term "prevention and/or treatment", when relating to infection of egg drop syndrome virus, refers to inhibition of replication and spread of the egg drop syndrome virus or prevention of the egg drop syndrome virus from colonizing its host, and alleviation of disease or symptoms of illness of the egg drop syndrome virus. If the viral load is reduced, the severity of the illness is reduced, and/or the food intake and/or growth are increased, then it can be considered that the treatment has achieved a therapeutic effect.

The description of the present disclosure is further provided as follows with reference to the specific embodiments, and features and advantages of the present disclosure will become more apparent from the following description. However, these embodiments are only exemplary, but not forming any limitation to the scope of the present disclosure. It should be understood by a person skilled in the art that modifications or alternatives to details and forms of the technical solution of the present disclosure without deviation from the spirit and scope of the present disclosure will be allowed, while those modification and alternatives should all fall within the scope of the present disclosure.

The chemical reagents used in the examples of the present disclosure are of analytical grade and are purchased from Sinopharm Group Co. Ltd.

In order to make the present disclosure more understandable, the present disclosure will be further described with reference to specific embodiments. The experimental methods described in the present disclosure are conventional methods unless otherwise specified. The biological materials are commercially available unless otherwise specified.

Example 1 Construction of Expression Vector of pET28a-EDSV-Fiber

1. Extraction of EDSV DNA

A plasmid extraction kit was purchased from TIANGEN BIOTECH; T4 DNA Ligase was purchased from BioLab; pET28a plasmid was purchased from Novagen; an agarose gel recovery kit was purchased from Tianze Biotech, other reagents are analytically pure.

According to the instruction of the viral DNA extraction kit, 0.2 ml of the egg drop syndrome virus was placed in a 1.5 ml sterile centrifuge tube, and added with 0.4 ml of VB buffer, mixed well by vortexing, and let stand at room temperature for 10 minutes. 0.45 ml of AD buffer was added in the above sample solution and mixed strongly. The VB column was placed in a 2 ml collection tube and 0.6 ml of the mixture was added to the VB column, which was then centrifuged at 14,000 g for 1 minute. The remaining mixture was added to the VB column which was then centrifuged at 14,000 g for 1 minute, the 2 ml collection tube was discarded and the VB column was placed into a new 2 ml collection tube. 0.4 ml of W1 buffer was added into the VB column which was then centrifuged at 14000 g for 30 seconds, add 0.6 ml Wash buffer in VB column, centrifuged at 14000 g for 30 seconds and centrifuged without adding any buffer for 3 minutes. The VB column is placed into a new 1.5 ml EP tube. 50 μl RNase free water was added to the center of membrane and let sit for 3 minute, centrifuged at 14000 g for 1 minute and the centrifuged liquid was DNA genome.

2. Amplification of Fiber-2 Protein Gene

Oligonucleotide primers were synthesized based on the conserved region sequences at the 5' and 3' ends of the Fiber protein gene and subjected to PCR. Primer sequences are shown in Table 1.

1. Primers for the Amplification of the Fiber Protein gene

| | |
|---|---|
| Fiber-F (SEQ ID NO. 3) | atgaagcgactacggttggaccctg |
| Fiber-R (SEQ ID NO. 4) | ctactgtgctccaacatatgtaaag |

The PCR product was sent to Invitrogen Corporation for sequencing, and codon optimization was performed to the Fiber protein gene according to the sequencing result, the sequence of the optimized Fiber protein gene is shown in SEQ ID NO. 1.

3. Construction of Expression Vector

The optimized Fiber protein gene was sent to GENEWIZ, Inc. for full sequence synthesis and linked into pET28a plasmid respectively. The linked plasmid and molecular chaperone plasmid were co-transformed into *E. coli* BL21 (DE3). The single clone was picked up and cultured in LB medium containing 100 μg/ml of kanamycin and 20 μg/ml of chloramphenicol overnight. The plasmid was extracted and sequenced. The positive clone was pET28a-EDSV-Fiber/pG-Tf2 expression strain.

Example 2 Preparation of Fiber Protein

The pET28a-EDSV-Fiber/pG-Tf2/*E. coli* BL21(DE3) strain prepared in Example 1 was inoculated into LB medium containing 50-100 μg/ml of kanamycin and 20 μg/ml of chloramphenicol at an inoculum amount of 1% (V/V), and cultured with shaking at 37° C.; meanwhile the LB medium also contains 5-10 ng/ml of tetracycline for inducible expression of molecular chaperone protein. When $OD_{600}$=0.4-0.6, the sample was placed at 28° C. for 30 minutes. Isopropyl-β-D-thiogalactopyranoside (IPTG) was added to a final concentration of 0.1-1.0 mM and the sample was cultured with shaking at 28° C. for 24 hours. After cultivation, the bacteria were harvested and resuspended in PBS (sodium chloride, 8 g, potassium chloride, 0.2 g, disodium hydrogen phosphate, 1.44 g, potassium dihydrogen phosphate, 0.24 g, adjusted to pH 7.4 with a final volume of 1 L), centrifuged after ultrasonic decomposition and the supernatant was obtained. The expression product had a higher content of the soluble target protein, the amount of expression of the soluble Fiber protein could reach up to 30% of the total bacterial protein, the HA titer of the Fiber protein reached 1:512, and the endotoxin had a content of $0.51\times10^5$ EU/ml.

Example 3 Clearance of Endotoxin in the Fiber Protein Expressed in *E. coli*

0.5 ml of the solution to be treated and Triton X-114 (5 μl) at a final concentration of 1% (v/v) were added to a 1.5 ml centrifuge tube and vortexed. The sample was placed on ice for 5 minutes. After vortexing the cooled sample, the centrifuge tube was immediately put in a 37° C. water bath for 5 min to create new two phases. Then, the sample was centrifuged at 37° C. for 60 seconds. After centrifugation, the target protein will remain in the upper layer, while the endotoxin-containing detergent will remain in the shape of an oil droplet at the bottom of the centrifuge tube. The entire operation for clearing endotoxin went through 3 cycles. It was measured that the HA titer of the Fiber protein reached 1:512, and the content of the endotoxin had been reduced into $0.009 \times 10^5$ EU/ml.

The results showed that Triton X-114 could eliminate the residual endotoxin in the recombinant protein and had no effect on the immunogenicity of the Fiber protein.

Example 4 Preparation of Subunit Vaccine of the Fiber Protein of Egg Drop Syndrome Virus The fiber protein purified according to the method of Example 3 was slowly added to the white oil adjuvant, while the motor was started to stir the mixture at 17500 r/min for 5 min. 1% thimerosal solution was added before termination of stirring to a final concentration of 0.01%. The component ratios are shown in Table 2.

TABLE 2

Component ratios of the subunit vaccine of the Fiber protein of egg drop syndrome virus

| Component | Vaccine 1 | Vaccine 2 | Vaccine 3 |
| --- | --- | --- | --- |
| Fiber protein (HA titer) | 1:32 | 1:64 | 1:128 |
| White oil adjuvant (v/v %) | 66% | 66% | 66% |

Example 5 Safety Test of the Subunit Vaccine of the Fiber Protein of Egg Drop Syndrome Virus 60 21-day-old SPF chickens were divided into 4 groups, that is to say, 15 chickens per group, the chickens in groups 1-3 were immunized by subcutaneous injection in necks with corresponding vaccine 1, vaccine 2, vaccine 3 prepared in Example 4, respectively, at an immune amount of 0.1 ml, and the chickens in group 4 were injected with 0.1 ml of physiological saline solution by subcutaneous injection, as a blank control. The chickens were fed under the same conditions, and observed starting from the third week after immunization for clinical symptoms, weight gain rate and mortality. Five chickens were dissected respectively at 3 weeks, 4 weeks and 5 weeks to observe whether the inoculation site formed gross lesions. The results showed (see Table 3, Table 4) that, no clinical symptoms and death could be observed in the vaccination groups (vaccine 1-3), in addition, the weight gain rate of the vaccination groups and the control group showed no significant difference, and no granulomas were formed, indicating that it was safe and would not have effect on weight gaining to immunize chickens with the subunit vaccine of the Fiber protein of egg drop syndrome virus of the present disclosure.

TABLE 3

Clinical symptoms and number of deaths for safety test of the subunit vaccine of the Fiber protein of egg drop syndrome virus

| | | Clinical symptoms and number of deaths after immunization | |
| --- | --- | --- | --- |
| Group | Number of chickens | Clinical Symptoms | deaths |
| 1 | 15 | 0/15 | 0/15 |
| 2 | 15 | 0/15 | 0/15 |
| 3 | 15 | 0/15 | 0/15 |
| 4 | 15 | 0/15 | 0/15 |

TABLE 4

Chicken weight change and formation of granulomas for safety test of the subunit vaccine of the Fiber protein of egg drop syndrome virus

| | | Weight (g, mean ± SD) | | Formation of granulomas after immunization | | |
| --- | --- | --- | --- | --- | --- | --- |
| Group | Number of chickens | Before immunization | End up at the third week after immunization | 3 weeks | 4 weeks | 5 weeks |
| 1 | 15 | 323 ± 17.1 | 579 ± 19.7 | 0/5 | 0/5 | 0/5 |
| 2 | 15 | 325 ± 16.8 | 578 ± 17.5 | 0/5 | 0/5 | 0/5 |
| 3 | 15 | 327 ± 15.9 | 576 ± 16.6 | 0/5 | 0/5 | 0/5 |
| 4 | 15 | 328 ± 19.2 | 579 ± 20.0 | 0/5 | 0/5 | 0/5 |

Example 6 Immunogenicity Test of the Subunit Vaccine of the Fiber Protein of Egg Drop Syndrome Virus in SPF Chickens 40 21-day-old SPF chickens were divided into 4 groups, that is to say, 10 chickens per group, the chickens in groups 5-7 were immunized by subcutaneous injection in necks with corresponding vaccines 1-3 prepared in Example 4, respectively, at an immune amount of 0.5 ml, and the chickens in group 8 were injected with 0.5 ml of physiological saline solution by subcutaneous injection, as a blank control. All experimental chickens were fed in isolation. Before immunization and on the 21st day after immunization, blood sample was taken from each of the chickens and the corresponding serum was separated and the HI titer of the egg drop syndrome virus antibody in each serum was determined. The results are shown in Table 5

TABLE 5

Results of immunogenicity test of the subunit vaccine of the Fiber protein of egg drop syndrome virus in SPF chickens

| | | | Results of determining HI antibody titers (log2) | |
| --- | --- | --- | --- | --- |
| Group | Immune dose (ml per chicken) | Number of chickens | Before immunization | On the 21st day after immunization |
| 5 | 0.5 | 10 | 0 | 9.5 |
| 6 | 0.5 | 10 | 0 | 10.2 |
| 7 | 0.5 | 10 | 0 | 10.8 |
| 8 | 0.5 | 10 | 0 | 0 |

The results showed that the HI antibody titer in the 8th group, i.e. control group, on Day 21 after immunization was 0, while the groups 5-7, immunization groups all had a relatively higher HI antibody titer in the immunized chickens. The results showed that the subunit vaccine of the Fiber protein of egg drop syndrome virus with an HI tier that was not less than 1:32 could produce relatively higher HI antibody titer and could achieve effective immune protection for chickens.

Example 7 Immunogenicity Test of the Subunit Vaccine of the Fiber Protein of Egg Drop Syndrome Virus in Layers 40 115-day-old Hy-Line Brown chickens were divided into 4 groups, that is to say, 10 chickens per group, the chickens in groups 9-11 were immunized by subcutaneous injection in necks with corresponding vaccines 1-3 prepared in Example 4, respectively, at an immune amount of 0.5 ml, and the chickens in group 12 were injected with 0.5 ml of physiological saline solution by subcutaneous injection, as a blank control. Before immunization and on the 21st day after immunization, blood sample was taken from each of the chickens and the corresponding serum was separated and HI titer of the egg drop syndrome virus antibody in each serum was determined. When the laying rate reached up to about 90% (6 weeks after immunization), all four groups of chickens were challenged with virulent AV 127 strains, each chicken took 1 ml of 10-fold diluted virus orally, the virus content was $10^{6.5} EID_{50}$, the chickens were observed for 6 weeks after challenge with respect to feeding, spirit, stool and other conditions, the egg-laying numbers were recorded and the egg-laying rates were calculated. The results are shown in Table 6

TABLE 6

Results of immunogenicity test of the subunit vaccine of the Fiber protein of egg drop syndrome virus in layers

| Group | Immune dose (ml per chicken) | Number of chickens | Results of determining HI antibody titer (log2) | | Egg-laying rates | | |
|---|---|---|---|---|---|---|---|
| | | | Before immunization | On the 21st day after immunization | Before challenge | Week 3 after challenge | Week 6 after challenge |
| 9 | 0.5 | 10 | 0 | 9.4 | 89.1 | 91.5 | 90.7 |
| 10 | 0.5 | 10 | 0 | 9.7 | 91.0 | 89.8 | 91.2 |
| 11 | 0.5 | 10 | 0 | 10.2 | 90.5 | 91.4 | 90.2 |
| 12 | 0.5 | 10 | 0 | 0 | 90.1 | 47.4 | 70.5 |

The results showed that the titer of HI antibody of the 12th group i.e. control group on the 21st day after immunization was 0, and the egg-laying rate of the chickens in the control group decreased after challenge, and in the third week after challenge, the egg-laying rate dropped from about 90% to 47% or so, while the shell color faded and soft-shell eggs, shell-less eggs and deformed eggs, and the like were laid; in the sixth week after challenge, the egg-laying rate was about 70%, but still not back to a normal level. The immunized groups from group 9 to group 11 all had higher HI antibody titers in immunized chickens, and there was almost no change in egg-laying rate after challenge, indicating that the chickens immunized with the subunit vaccine of the Fiber protein of egg drop syndrome virus having a HA titer no less than 1:32, all produced relatively higher HI antibody titers. The Fiber protein antigens of the present disclosure had good immunogenicity and could provide effective immune protection for ducks, even at a low content.

Example 8 Immunogenicity Test of the Subunit Vaccine of the Fiber Protein of Egg Drop Syndrome Virus in Cherry Valley Ducks 40 42-day-old Cherry Valley ducks were divided into 4 groups, that is to say, 10 ducks per group, the ducks in groups 13-15 were immunized by subcutaneous injection in necks with corresponding vaccines 1-3 prepared in Example 4, respectively, at an immune amount of 0.5 ml, and the ducks in group 16 were injected with 0.5 ml of physiological saline solution by subcutaneous injection, as a blank control. All experimental ducks were fed in isolation. Before immunization and on the 21st day after immunization, blood sample was taken from each of the ducks and the corresponding serum was separated and the HI titer of the egg drop syndrome virus antibody in each serum was determined. The results are shown in Table 7.

Example 7 Results of Immunogenicity Test of the Subunit Vaccine of the Fiber Protein of Egg Drop Syndrome Virus in Cherry Valley Ducks

| Group | Immune dose (ml per chicken) | Number of ducks | Results of determining HI antibody titers (log2) | |
|---|---|---|---|---|
| | | | Before immunization | On the 21st day after immunization |
| 13 | 0.5 | 10 | 0 | 9.3 |
| 14 | 0.5 | 10 | 0 | 10.2 |
| 15 | 0.5 | 10 | 0 | 10.6 |
| 16 | 0.5 | 10 | 0 | 0 |

The results showed that the HI antibody titer in the 16th group, i.e. control group, on Day 21 after immunization was 0, while the immunization groups 13-15 all had a relatively higher HI antibody titer in the immunized ducks. The results showed that the subunit vaccine of the Fiber protein of egg drop syndrome virus with an HI tier that is not less than 1:32 could produce relatively higher HI antibody titer. The Fiber protein antigens of the present disclosure had good immunogenicity and could provide effective immune protection for ducks, even at a low content.

Example 9 Broad-Spectrum Protection Test of the Subunit Vaccine of the Fiber Protein of Egg Drop Syndrome Virus 100 120-day-old Hy-Line Brown layers were divided into 10 groups, that is to say, 10 chickens per group, the chickens in groups 17-21 were immunized by subcutaneous injection in necks with corresponding vaccine 1 prepared in Example 4, respectively, at an immune amount of 0.5 ml, and the chickens in groups 22-26 were injected with 0.5 ml of physiological saline solution by subcutaneous injection. Before immunization and on the 21st day after immunization, blood sample was taken from each of the chickens and the corresponding serum was separated and HI titer of the egg drop syndrome virus antibody in each serum was determined. When the laying rate reached up to about 90% (6 weeks after immunization), the experimental chickens from groups 17 and 22 were challenged with the virulent egg drop syndrome virus HN09 strain newly isolated from Henan; the experimental chickens from groups 18 and 23 were challenged with the virulent egg drop syndrome virus SD02 strain newly isolated from Shandong; the experimental chickens from groups 19 and 24 were challenged with the virulent egg drop syndrome virus GD04 strain newly isolated from Guangdong; the experimental chickens from groups 20 and 25 were challenged with the virulent egg drop syndrome virus LN02 strain newly isolated from Liaoning; the experimental chickens from groups 21 and 26 were challenged with the virulent egg drop syndrome virus SC01 strain newly isolated from Sichuan; each chicken took 1 ml of 10-fold diluted virus orally, the virus content was $10^{6.5} EID_{50}$, the chickens were observed for 6 weeks after challenge in terms of feeding, spirit, stool and other conditions, the egg-laying numbers were recorded and the egg-laying rates were calculated. The results are shown in Table 8.

TABLE 8

Results of broad-spectrum protection test of the subunit vaccine of the Fiber protein of egg drop syndrome virus

| Group | Immune dose (ml per chicken) | Number of chickens | Results of determining HI antibody titer (log2) Before immu-nization | On the 21st day after immu-nization | Egg-laying rates Before chal-lenge | Week 3 after chal-lenge | After chal-lenge Week 6 |
|---|---|---|---|---|---|---|---|
| 17 | 0.5 | 10 | 0 | 5.4 | 90.3 | 90.5 | 91.0 |
| 18 | 0.5 | 10 | 0 | 5.5 | 90.4 | 90.6 | 90.8 |
| 19 | 0.5 | 10 | 0 | 5.5 | 90.2 | 90.6 | 91.2 |
| 20 | 0.5 | 10 | 0 | 5.5 | 90.2 | 91.0 | 91.2 |
| 21 | 0.5 | 10 | 0 | 5.4 | 90.4 | 90.6 | 91.0 |
| 22 | 0.5 | 10 | 0 | 0 | 90.5 | 45.4 | 68.6 |
| 23 | 0.5 | 10 | 0 | 0 | 90.4 | 44.4 | 66.2 |
| 24 | 0.5 | 10 | 0 | 0 | 90.6 | 43.6 | 65.4 |
| 25 | 0.5 | 10 | 0 | 0 | 90.3 | 44.1 | 67.0 |
| 26 | 0.5 | 10 | 0 | 0 | 90.5 | 44.6 | 65.4 |

The results showed that the titers of HI antibody of control groups 22-26 on the 21st day after immunization were 0, and the egg-laying rate of the chickens decreased after challenge, and in the third week after challenge, the egg-laying rate dropped from 90.3%-90.6% to 43.6%-45.4%, while the shell color faded and soft-shell eggs and shell-less eggs and the like were laid; in the sixth week after challenge, the egg-laying rate returned to 65.4%-68.6%, but still not back to a normal level. However, the immunization groups 17-21 all had relatively higher HI antibody titers in immunized chickens, and there was almost no change in egg-laying rate after challenge, indicating that the chickens immunized with the subunit vaccine of the Fiber protein of egg drop syndrome virus having a HA titer of no less than 1:32, all produced relatively higher HI antibody titers. And the antigen had a broad spectrum and could provide effective immune protection for chickens challenged by wild strains of egg drop syndrome virus from different regions. The egg-laying rate would not be affected by infection of wild strain of egg drop syndrome virus.

Example 10 Preparation of Antigens of Newcastle Disease Virus

Newcastle disease virus (genotype VII), N7 strain deposited in China Center for Type Culture Collection on Oct. 19, 2015 with an accession number CCTCC NO: V201545 and a deposition address that is Wuhan University, Wuhan, China, was diluted appropriately ($10^{-4}$ or $10^{-5}$) with sterile saline so as to inoculate susceptible chicken embryos which are 10-11 days old at 0.1 ml per embryo and the chicken embryos were placed at 37° C. after inoculation for subsequent incubation. Allantoic fluid was harvested from chicken embryos which were died within 48 to 120 hours after inoculation or survived at 120 hours after inoculation, the virus content determined was $10^{8.0} EID_{50}/0.1$ ml. Formaldehyde solution with a final concentration of 0.1% (v/v) was added into the sample which is then placed at 37° C. to be inactivated, and stirred once every 4-6 hours during the process, and stored after 16 hours of complete inactivation.

Example 11 Preparation of Antigens of Avian Influenza Virus

H9 subtype of avian influenza virus SZ strain (disclosed in Chinese patent application CN103789272A) was picked as a virus species and diluted with sterile saline to $10^{-3}$ (0.1 ml of virus solution was added to 0.9 ml sterile saline, and then diluted 2 more times after shaking and mixing). The diluted virus solution was inoculated into 10-day-old susceptible chicken embryos (hatched from SPF hatching eggs purchased from Beijing Meiliyaweitong Experimental Animal Technology Co., Ltd) via the allantoic cavity at 0.1 ml (containing $10^5 EID_{50}$) per embryo. The pinhole was sealed after inoculation, and the chicken embryos were placed at 36-37° C. for subsequent incubation. It was not necessary to turn over the chicken embryos. After 96 hours, the chicken embryos were removed and placed upright with upward gas chambers, and cooled at 2-8° C. for 12-24 hours. Allantoic fluid was harvested from the cooled chicken embryos. The virus content determined was $10^{8.5} EID_{50}/0.1$ ml. Formaldehyde solution with a final concentration of 0.1% (v/v) was added into the sample which is then placed at 37° C. to be inactivated, and stirred once every 4-6 hours during the process, and stored after 24 hours of complete inactivation.

Example 12 Preparation of Antigens of Avian Infectious Bronchitis Virus

Avian infectious bronchitis virus M41 strain (purchased from the China Veterinary Drug Administration) was diluted appropriately (to $10^{-2}$ or $10^{-3}$) with sterile saline so as to inoculate susceptible chicken embryos which are 10-11 days old at 0.1 ml per embryo and the chicken embryos placed at 36-37° C. after inoculation for subsequent incubation. Allantoic fluid was harvested from chicken embryos which were died within 24 to 48 hours after inoculation or survived 24-48 hours after inoculation, the virus content determined was $10^{6.0}$ $EID_{50}/0.1$ ml. Formaldehyde solution with a final concentration of 0.1% (v/v) was added into the sample which is then placed at 37° C. to be inactivated, and stirred once every 4-6 hours during the process, and stored after 16 hours of complete inactivation.

Example 13 Preparation of Antigens of Infectious Bursal Disease Virus

1. Preparation of VP2 cDNA

The IBDV RNA was extracted from the bursa of Fabricius of SPF chickens infected with very virulent IBDV Chengdu strain by virus RNA extraction kit and reverse transcribed with random primers. Oligonucleotide primers were synthesized based on the conserved region sequences at the 5 'and 3' ends of the VP2 protein gene. The sequence of the synthesized oligonucleotide primers are shown in Table 1. PCR amplification was conducted, and the product was recovered by the agarose gel recovery kit and stored at −20° C.

TABLE 9

Primers for amplification of gene of IBDV VP2 protein

| | |
|---|---|
| VP2-EcoR1-F (SEQ ID NO. 5) | CCGGAATTCATGACAAACCTGCAAGATCAAAC |
| VP2-Sal1-R (SEQ ID NO. 6) | ACGCGTCGACTTACCTTAGGGCCCGGATTATGT |

2. Construction of pCold III_VP2/*E. coli* BL21(DE3) Strain

The VP2 cDNA prepared above was double-digested, and the digested fragment was ligated into the pCold III vector. The ligated product was directly transformed into *E. coli* BL21 (DE3) and spread on a solid LB medium containing 100 μg of ampicillin and cultured overnight, the colonies grew were the pCold III_VP2/*E. coli* BL21 (DE3) strain.

3. Preparation of Infectious Bursal Disease Virus VP2 Protein

The strain was cultured in a culture tank with natural ventilation, which was filled with 70% culture medium and peanut oil defoamer according to the volume. After sterilization, the seed solution of pColdIII_VP2/*E. coli* BL21 (DE3) strain was inoculated at 2%-4% of the amount of culture medium and cultured at 37° C. 0.2 mol/L α-lactose was added in when the $OD_{600}$ value of the solution reached 0.6-1.0, so that its final concentration reached 0.02 mol/L, then the solution was cultured for 5-8 h.

After cultivation, the bacteria were collected by centrifugation, resuspended, ultrasonicated, and centrifuged to collect the supernatant. After precipitation with ammonium sulfate, VP2 protein liquid was collected.

Example 14 Preparation of Antigens of Fowl Adenovirus

1. Preparation of Fiber-2 cDNA

FADV DNA was extracted from the FAV-HN strain of fowl aviadenovirus according to the manual of the virus RNA extraction kit. The FAV-HN strain (F owl aviadenovirus, strain FAV-HN) has been deposited in the China Center for Type Culture Collection on Feb. 29, 2016, of which the accession number is CCTCC NO. V 201609 and the address is Wuhan University, Wuhan, China. Oligonucleotide primers were synthesized based on the conserved region sequences at the 5' and 3' ends of the Fiber-2 protein gene. The sequences of the synthesized oligonucleotide primers are shown in Table 10. PCR amplification was conducted, and the product was recovered by the agarose gel recovery kit and stored at −20° C.

TABLE 10

Primers for amplification of gene of the Fiber-2 protein of Fowl aviadenovirus

| | |
|---|---|
| Fiber-2-F (SEQ ID NO. 7) | CTCCGGGCCCCTAAAAG |
| Fiber-2-R (SEQ ID NO. 8) | CGGGACGGAGGCCGC |

2. Construction of Expression Vector

The optimized Fiber-2 protein gene was sent to GENEWIZ, Inc. for full sequence synthesis and linked into pET28a plasmid respectively. The linked plasmid and molecular chaperone plasmid were co-transformed into *E. coli* BL21 (DE3). The single clone was picked up and cultured in LB medium containing 100 μg/ml of kanamycin overnight. The plasmid was extracted and sequenced. The positive clone was pET28a-FADV-Fiber-2 expression strain.

3. Preparation of Fiber-2 Protein

The pET28a-FADV-Fiber-2/*E. coli* BL21(DE3) strain prepared in Example 1 was inoculated into LB medium containing 50-100 μg/ml of kanamycin at an inoculum amount of 1% (V/V), and cultured with shaking at 37° C. When $OD_{600}$=0.4-0.6, the sample was placed at 28° C. for 30 minutes. Isopropyl-β-D-thiogalactopyranoside (IPTG) was added to a final concentration of 0.1 mM and the sample was cultured with shaking at 28° C. for 24 hours.

After cultivation, the bacteria were harvested and resuspended in PBS (sodium chloride, 8 g, potassium chloride, 0.2 g, disodium hydrogen phosphate, 1.44 g, potassium dihydrogen phosphate, 0.24 g, adjusted to pH 7.4 with a final volume of 1 L), centrifuged after ultrasonic decomposition and the supernatant was obtained. The Fiber-2 protein solution was collected.

Example 15 Preparation of Combined Vaccine of Egg Drop Syndrome Virus

The Fiber protein purified according to Example 3 was mixed with antigen of Newcastle disease virus prepared according to Example 10, antigen of avian influenza virus prepared according to Example 11, antigen of avian infectious bronchitis virus prepared according to Example 12, antigen of infectious bursal disease virus prepared according to Example 13, and antigen of fowl adenovirus prepared according to Example 14 in a certain ratio, respectively, and added to the white oil adjuvant, while the motor was started to stir the mixture at 17500 r/min for 5 min. 1% thimerosal solution was added before termination of stirring to a final concentration of 0.01%. The component ratios are shown in Table 11, 12, 13 and 14.

TABLE 11

Component ratios of egg drop syndrome virus two-combined vaccine

| Component | Vaccine 4 | Vaccine 5 | Vaccine 6 | Vaccine 7 | Vaccine 8 |
|---|---|---|---|---|---|
| Fiber protein (HA titer) | 1:32 | 1:64 | 1:128 | 1:32 | 1:64 |
| Antigen of N7a strain ($EID_{50}$/0.1 ml) | $10^{8.0}$ | — | — | — | — |
| Antigen of SZ strain ($EID_{50}$/0.1 ml) | — | $10^{8.0}$ | — | — | — |
| Antigen of M41 strain ($EID_{50}$/0.1 ml) | — | — | $10^{6.0}$ | — | — |
| VP2 protein (AGP titer) | — | — | — | 1:16 | — |
| Fiber-2 protein (AGP titer) | — | — | — | — | 1:4 |
| White oil adjuvant (V/V %) | 66% | 66% | 66% | 66% | 66% |

TABLE 12

Component ratios of egg drop syndrome virus three-combined vaccine

| Component | Vaccine 9 | Vaccine 10 | Vaccine 11 | Vaccine 12 |
|---|---|---|---|---|
| Fiber protein (HA titer) | 1:32 | 1:64 | 1:128 | 1:32 |
| Antigen of N7a strain ($EID_{50}/0.1$ ml) | $10^{8.0}$ | $10^{8.0}$ | $10^{8.0}$ | $10^{8.0}$ |
| Antigen of SZ strain ($EID_{50}/0.1$ ml) | $10^{8.0}$ | — | — | — |
| Antigen of M41 strain ($EID_{50}/0.1$ ml) | — | $10^{6.0}$ | — | — |
| VP2 protein (AGP titer) | — | — | 1:16 | — |
| Fiber-2 protein (AGP titer) | — | — | — | 1:4 |
| White oil adjuvant (V/V %) | 66% | 66% | 66% | 66% |

TABLE 13

Component ratios of egg drop syndrome virus four-combined vaccine

| Component | Vaccine 13 | Vaccine 14 | Vaccine 15 | Vaccine 16 | Vaccine 17 |
|---|---|---|---|---|---|
| Fiber protein (HA titer) | 1:32 | 1:64 | 1:128 | 1:32 | 1:64 |
| Antigen of N7a strain ($EID_{50}/0.1$ ml) | $10^{8.0}$ | $10^{8.0}$ | $10^{8.0}$ | $10^{8.0}$ | $10^{8.0}$ |
| Antigen of SZ strain ($EID_{50}/0.1$ ml) | $10^{8.0}$ | — | — | $10^{8.0}$ | $10^{8.0}$ |
| Antigen of M41 strain ($EID_{50}/0.1$ ml) | $10^{6.0}$ | $10^{6.0}$ | $10^{6.0}$ | — | — |
| VP2 protein (AGP titer) | — | 1:16 | — | 1:16 | — |
| Fiber-2 protein (AGP titer) | — | — | 1:4 | — | 1:4 |
| White oil adjuvant (V/V %) | 66% | 66% | 66% | 66% | 66% |

TABLE 14

Component ratios of egg drop syndrome virus five-combined vaccine

| Component | Vaccine 18 | Vaccine 19 |
|---|---|---|
| Fiber protein (HA titer) | 1:32 | 1:64 |
| Antigen of N7a strain ($EID_{50}/0.1$ ml) | $10^{8.0}$ | $10^{8.0}$ |
| Antigen of SZ strain ($EID_{50}/0.1$ ml) | $10^{8.0}$ | $10^{8.0}$ |
| Antigen of M41 strain ($EID_{50}/0.1$ ml) | $10^{6.0}$ | $10^{6.0}$ |
| VP2 protein (AGP titer) | 1:16 | — |
| Fiber-2 protein (AGP titer) | — | 1:4 |
| White oil adjuvant (V/V %) | 66% | 66% |

Example 16 Immunogenicity Test of the Combined Vaccine of Egg Drop Syndrome Virus 1. Immunogenicity Test of Egg Drop Syndrome Virus Part 170 21-day-old SPF chickens were divided into 17 groups, that is to say, 10 chickens per group, the chickens in groups 27-42 were immunized by subcutaneous injection in necks with corresponding vaccines 4-19 prepared in Example 15, respectively, at an immune amount of 0.5 ml, and the chickens in group 43 were injected with 0.5 ml of physiological saline solution by subcutaneous injection, as a blank control. All experimental chickens were fed in isolation. On the 21st day after immunization, blood sample was taken from each of the chickens and the corresponding serum was separated and HI titer of the egg drop syndrome virus antibody in each serum was determined. The results are shown in Table 15.

TABLE 15

Results of immunogenicity test of the egg drop syndrome virus part of the combined vaccine of egg drop syndrome virus

| Group | Immune dose (ml per chicken) | Number of chickens | Before immunization | On the 21st day after immunization |
|---|---|---|---|---|
| 27 | 0.5 | 10 | 0 | 9.9 |
| 28 | 0.5 | 10 | 0 | 10 |
| 29 | 0.5 | 10 | 0 | 10.2 |
| 30 | 0.5 | 10 | 0 | 9.5 |
| 31 | 0.5 | 10 | 0 | 9.8 |
| 32 | 0.5 | 10 | 0 | 10.4 |
| 33 | 0.5 | 10 | 0 | 10.2 |
| 34 | 0.5 | 10 | 0 | 9.9 |
| 35 | 0.5 | 10 | 0 | 10 |
| 36 | 0.5 | 10 | 0 | 9.5 |
| 37 | 0.5 | 10 | 0 | 9.7 |
| 38 | 0.5 | 10 | 0 | 9.6 |
| 39 | 0.5 | 10 | 0 | 9.9 |
| 40 | 0.5 | 10 | 0 | 10.1 |
| 41 | 0.5 | 10 | 0 | 9.4 |
| 42 | 0.5 | 10 | 0 | 10.3 |
| 43 | 0.5 | 10 | 0 | 0 |

(Results of determining HI antibody titers (log2))

The results showed that the groups immunized with vaccines 4-19 produced relatively higher HI antibody titers on the 21st days after immunization, which could effectively prevent the outbreak of egg drop syndrome among chicken flocks. It is shown that the oil-emulsion combined vaccine, in which the Fiber protein of egg drop syndrome virus provided by the present disclosure was prepared as an antigen, could provide complete protection for the chickens.

2. Immunogenicity Test of Newcastle Disease Virus Part 130 21-day-old SPF chickens were divided into 13 groups, that is to say, 10 chickens per group, the chickens in groups 44-55 were immunized by subcutaneous injection in necks with corresponding vaccines 4, and 9-19 prepared in Example 15, respectively, at an immune amount of 20 µl, and the chickens in group 44 were injected with 20 µl of physiological saline solution by subcutaneous injection, as a blank control of challenge. All the experimental chickens were fed in isolation. On the 21st day after immunization, the blood samples of the immunized chicken in groups 44-55 together with the control chicken in the 56th group were collected and the corresponding serums were separated. HI antibody of the Newcastle disease virus was detected, meanwhile the chicken were challenged by intramuscular injection of the virus solution of virulent Newcastle disease HN1101 strain and then were observed for 14 days. The numbers of incidence and deaths and protection rates were recorded. The results are shown in Table 16.

TABLE 16

Results of immunogenicity test of the Newcastle disease virus part of the combined vaccine of egg drop syndrome virus

| Group | Immune dose (μl per chicken) | Number of chickens | Results of determining HI antibody titer (log2) | | Results of challenge | | |
|---|---|---|---|---|---|---|---|
| | | | Before immunization | Day 21 after immunization | Number of incidence | Number of deaths | Protection rate |
| 44 | 20 | 10 | 0 | 8.3 | 0/10 | 0/10 | 100% |
| 45 | 20 | 10 | 0 | 8.0 | 0/10 | 0/10 | 100% |
| 46 | 20 | 10 | 0 | 8.1 | 0/10 | 0/10 | 100% |
| 47 | 20 | 10 | 0 | 8.2 | 0/10 | 0/10 | 100% |
| 48 | 20 | 10 | 0 | 8.2 | 0/10 | 0/10 | 100% |
| 49 | 20 | 10 | 0 | 8.1 | 0/10 | 0/10 | 100% |
| 50 | 20 | 10 | 0 | 8.0 | 0/10 | 0/10 | 100% |
| 51 | 20 | 10 | 0 | 8.0 | 0/10 | 0/10 | 100% |
| 52 | 20 | 10 | 0 | 8.0 | 0/10 | 0/10 | 100% |
| 53 | 20 | 10 | 0 | 8.1 | 0/10 | 0/10 | 100% |
| 54 | 20 | 10 | 0 | 8.1 | 0/10 | 0/10 | 100% |
| 55 | 20 | 10 | 0 | 8.0 | 0/10 | 0/10 | 100% |
| 56 | 20 | 10 | 0 | 0 | 10/10 | 10/10 | 0 |

Note:
the HI antibody was determined as the geometric mean of the immunized chicken antibody.

The results showed that the groups immunized with vaccines 4, and 9-19 could all produce a relatively higher Newcastle antibody and compared with the control group, could provide complete protection against the virulent strain. It is shown that the oil-emulsion combined vaccine, in which the Newcastle disease virus N7a strain solution provided by the present disclosure was prepared as antigen, could provide complete protection for the chickens.

3. Immunogenicity Test of Avian Influenza Virus Part 80 21-day-old SPF chickens were divided into 8 groups, that is to say, 10 chickens per group, the chickens in groups 57-63 were immunized by subcutaneous injection in necks with corresponding vaccines 5, 9, 13, and 16-19 prepared in Example 15, respectively, at an immune amount of 0.3 ml, and the chickens in group 64 were injected with 0.3 ml of physiological saline solution by subcutaneous injection, as a blank control of challenge. All the experimental chickens were fed in isolation. On the 21st day after immunization, the blood samples of the immunized chicken in groups 57-63 together with the control chicken in the 64th group were collected and the corresponding serums were separated. HI antibody of the H9 subtype of avian influenza virus was detected. Meanwhile the chickens were challenged by intramuscular injection of the virus solution of SZ strain at 0.2 ml (containing $10^{7.0}$ $EID_{50}$) per chicken. On the 5th day after challenge, cloacal swabs were collected. 5 SPF chicken embryos of 10 to 11 days old were inoculated with the treated cloacal swab samples through the allantoic cavity. After incubating for 5 days, both dead embryos and live embryos should be assayed for agglutination titers of the erythrocyte in the chicken embryo solution. Among each five chicken embryos inoculated with one swab sample, as long as the agglutination titers of one chicken embryo solution was not less than 1:16 (micro-method), it could be determined as being positive virus isolation. The samples showing negative virus isolation should be re-determined after blind passage. There should be at least 9 chickens in the immunization group showing negative virus isolation; and there should be at least 4 chickens in the control group showing positive virus isolation. The results are shown in Table 17.

TABLE 17

Results of immunogenicity test of the avian influenza virus part of the combined vaccine of egg drop syndrome virus

| Group | Immune dose (ml per chicken) | Number of chickens | Results of determining HI antibody titer (log2) | | Results of challenge | |
|---|---|---|---|---|---|---|
| | | | Before immunization | Day 21 after immunization | isolation rate of virus | Protection rate |
| 57 | 0.3 | 10 | 0 | 8.9 | 0/10 | 100% |
| 58 | 0.3 | 10 | 0 | 8.5 | 0/10 | 100% |
| 59 | 0.3 | 10 | 0 | 8.6 | 0/10 | 100% |
| 60 | 0.3 | 10 | 0 | 8.6 | 0/10 | 100% |
| 61 | 0.3 | 10 | 0 | 8.5 | 0/10 | 100% |
| 62 | 0.3 | 10 | 0 | 8.7 | 0/10 | 100% |
| 63 | 0.3 | 10 | 0 | 8.8 | 0/10 | 100% |
| 64 | 0.3 | 10 | 0 | 0 | 10/10 | 0 |

Note:
the HI antibody was determined as the geometric mean of the immunized chicken antibody.

The results showed that the groups immunized with vaccines 5, 9, 13, and 16-19 could all produce a relatively higher avian influenza virus antibody on the 21st day after immunization and compared with the control group, could provide complete protection against the virulent strain. It is shown that the oil-emulsion combined vaccine, in which the avian influenza virus H9 subtype strain solution provided by the present disclosure was prepared as antigen, could provide complete protection for the chickens.

4. Immunogenicity Test of Avian Infectious Bronchitis Part 80 21-day-old SPF chicken were divided into 8 groups, 10 chickens per group, that is to say, the chickens in groups 65-71 were immunized by eye-drop and norse-drop inoculation with live vaccines (H120 strain) of avian infectious bronchitis, respectively, at an immune amount of 0.05 ml per chicken. On the 21st day after immunization, the blood samples of the immunized chicken in groups 65-71 together with the control chicken in the 72th group were collected and the corresponding serums were separated. Meanwhile, the chickens in groups 65-71 were immunized by subcutaneous injection in necks with corresponding vaccines 6, 10, 13, 14, 15, 18, and 19 prepared in Example 15, respectively, at an immune amount of 0.3 ml per chicken. On the 28st day after immunization, the blood samples of the immunized chicken in groups 65-71 together with the control chicken in the 72th group were collected and the corresponding serums were separated. The serum samples collected from the immunized chickens in groups 65-71 on the 21th day after first immunization of live vaccines and on the 28th day after immunization of inactivated vaccines (The serum samples were collected from the control chickens in group 72 at the same time) were detected for HI antibody titers. For the immunization groups, the geometric mean of the HI antibody titers in the serums of second immunization was not less than 4 times of the geometric mean the HI antibody titers in the serums of first immunization, and the geometric mean of the HI antibody titers in the non-immunization control group was not higher than 1:8 (micromethod). At the same time, the challenge experiment was conducted with virulent M41 strain of avian infectious bronchitis virus via norse-drop inoculation at $10^{3.0}$ $EID_{50}$ per chicken. The results are shown in Table 18.

TABLE 18

Results of immunogenicity test of the avian infectious bronchitis part of the combined vaccine of egg drop syndrome virus

| Group | Antibody titers for the first immunization | Antibody titers for the second immunization | Factors of antibody titers for the first immunization versus antibody titers for the second immunization | isolation rate of virus after challenge |
|---|---|---|---|---|
| 65 | 1:18.3 | 1:91.9 | 5.0 | 0/10 |
| 66 | 1:18.7 | 1:100.4 | 5.4 | 0/10 |
| 67 | 1:20.4 | 1:103.5 | 5.1 | 0/10 |
| 68 | 1:24.9 | 1:125.6 | 5.0 | 0/10 |
| 69 | 1:24.1 | 1:122.8 | 5.1 | 0/10 |
| 70 | 1:25.7 | 1:124.9 | 4.9 | 0/10 |
| 71 | 1:20.1 | 1:121.2 | 6.0 | 0/10 |
| 72 | ≤1:4 | ≤1:4 | — | 5/5 |

The results showed that the geometric means of the HI antibody titers in the serums of second immunization for vaccines 6, 10, 13, 14, 15, 18, and 19 were not less than 4 times of the geometric means of the HI antibody titers in the serums of first immunization, no virus was isolated from all of the tracheas of immunized chickens after challenge. The vaccines 6, 10, 13, 14, 15, 18, and 19 could provide complete protection against the virulent strain. It is shown that the oil-emulsion combined vaccine, in which the avian infectious bronchitis part strain solution provided by the present disclosure was prepared as antigen, could provide complete protection for the chickens.

5. Immunogenicity Test of Avian Infectious Bursal Disease Virus Part 60 21-day-old SPF chickens were divided into 6 groups, that is to say, 10 chickens per group, the chickens in groups 73-77 were immunized by subcutaneous injection in necks with corresponding vaccines 7, 11, 14, 16, and 18 prepared in Example 15, respectively, at an immune amount of 0.3 ml per chicken, and the chickens in group 78 were injected with 0.3 ml of physiological saline solution by subcutaneous injection, as a blank control of challenge. All experimental chickens were fed in isolation. On the 21st day after immunization, the chickens in groups 73-78 were challenged by eye-drop inoculation with 0.1 ml (actual virus content≥100 BID) of 100-fold dilution of virus solution of BC6-85 ((CVCC AV7 strain, purchased from the China Veterinary Drug Administration) of the avian infectious bursal disease. After challenge, clinical signs of the chickens were observed daily, and the numbers of incidence and deaths and protection rates were recorded. The survived chickens were killed after 72-96 hours, dissections were conducted respectively to observe lesions of the Bursa of Fabricus etc. There should be at least 8 normal chickens in the immunization groups showing negative lesions of the Bursa of Fabricus; and there should be at least 4 sick chickens in the control group showing significant lesions of the Bursa of Fabricus (e.g. one or more of lesions such as strip-like bleeding of breast or leg muscle, enlargement or shrinking of bursa of Fabricius, yellowing of bursa of Fabricius, jelly-like secretions within bursa of Fabricius). The results are shown in Table 19.

TABLE 19

Results of immunogenicity test of the avian infectious bursal disease virus part of the combined vaccine of egg drop syndrome virus

| Group | Immune dose (ml per chicken) | Number of chickens | Number of incidence | Protection rate |
|---|---|---|---|---|
| 73 | 0.3 | 10 | 0/10 | 100% |
| 74 | 0.3 | 10 | 0/10 | 100% |
| 75 | 0.3 | 10 | 0/10 | 100% |
| 76 | 0.3 | 10 | 0/10 | 100% |
| 77 | 0.3 | 10 | 0/10 | 100% |
| 78 | 0.3 | 10 | 10/10 | 0 |

The results showed that vaccines 7, 11, 14, 16, and 18 could provide complete protection against the virulent strain of the avian infectious bursal disease virus on Day 21 after immunization.

6. Immunogenicity Test of Fowl Adenovirus Part 60 21-day-old SPF chickens were divided into 6 groups, that is to say, 10 chickens per group, the chickens in groups 79-83 were immunized by subcutaneous injection in necks with corresponding vaccine 8, 12, 15, 17, and 19 prepared in Example 15, respectively, at an immune amount of 0.3 ml per chicken, and the chickens in group 84 were injected with 0.3 ml of physiological saline solution by subcutaneous injection, as a blank control. All experimental chicken were fed in isolation. On the 21st day after immunization, the chickens were challenged by intramuscular injection of the virus solution of FAV-HN strain and then were observed for 14 days. The numbers of incidence and deaths and protection rates were recorded. The results are shown in Table 20.

TABLE 20

Results of immunogenicity test of the fowl adenovirus part of the combined vaccine of egg drop syndrome virus

| Group | Immune dose (ml per chicken) | Number of chickens | Number of incidence | Number of deaths | Protection rate |
|---|---|---|---|---|---|
| 79 | 0.3 | 10 | 0/10 | 0/10 | 100% |
| 80 | 0.3 | 10 | 0/10 | 0/10 | 100% |
| 81 | 0.3 | 10 | 0/10 | 0/10 | 100% |
| 82 | 0.3 | 10 | 0/10 | 0/10 | 100% |
| 83 | 0.3 | 10 | 0/10 | 0/10 | 100% |
| 84 | 0.3 | 10 | 10/10 | 10/10 | 0 |

The results showed that the control group, the 84th group all died of the disease, while the immunization groups, groups 79-83 had better immune protection effect on the immunized chickens and the immunization effect was good. It is shown that the oil-emulsion combined vaccine, in which the avian influenza virus strain solution provided by the present disclosure was prepared as antigen, could provide complete protection for the chickens.

It is proved that the combined vaccine of egg drop syndrome virus provided by the disclosure can resist the invasion of related pathogens and shows good immunogenicity and can effectively control the epidemic of diseases associated with egg drop syndrome virus in China.

Example 17 Preparation of Subunit Vaccine of the Fiber Protein of Egg Drop Syndrome Virus The following primers were synthesized based on the Fiber protein gene of egg drop syndrome virus:
Fiber-F1:5-CATGCCATGGGCATGACAAGACC CGCAAAGCGACTACG GTTGGACCCT-3 (SEQ ID NO. 9),
Fiber-R1:5-CCGCTCGAGCTACTGTGCTC-CAACATATG-3 (SEQ ID NO. 10). The gene fragment of the Fiber protein gene of egg drop syndrome virus was obtained through PCR amplification.

The PCR product was sent to Invitrogen Corporation for sequencing, and the sequencing result is as shown in the sequence of SEQ ID NO. 2.

The PCR product was electrophoresed to recover the target fragments and these were ligated into pET28a plasmid. The linked plasmid and molecular chaperone plasmid were co-transformed into *E. coli* BL21 (DE3). The single clone was picked up and cultured in LB medium containing 100 μg/ml of kanamycin overnight. The plasmid was extracted and sequenced. The positive clone was pET28a-EDSV-Fiber expression strain.

The pET28a EDSV Fiber/*E. coli* BL21 (DE3) strain was inoculated into LB medium containing 50-100 μg/ml of kanamycin and 20 μg/ml of chloramphenicol at an inoculum amount of 1% (V/V), and cultured with shaking at 37° C. When $OD_{600}$=0.4-0.6, the sample was placed at 28° C. for 30 minutes. Isopropyl-β-D-thiogalactopyranoside (IPTG) was added to a final concentration of 0.1-1.0 mM and the sample was cultured with shaking at 28° C. for 24 hours. After cultivation, the bacteria were harvested and resuspended in PBS (sodium chloride, 8 g, potassium chloride, 0.2 g, disodium hydrogen phosphate, 1.44 g, potassium dihydrogen phosphate, 0.24 g, adjusted to pH 7.4 with a final volume of 1 L), centrifuged after ultrasonic decomposition and the supernatant was obtained. The expression product had a higher content of the soluble target protein, the amount of expression of the soluble Fiber protein could reach up to 32% of the total bacterial protein, the HA titer of Fiber protein reached 1:2048, and the endotoxin had a content of $0.49\times10^5$ EU/ml.

It was measured that the HA titer of Fiber protein reached 1:2048, and the content of the endotoxin had been reduced into $0.008\times10^5$ EU/ml.

The results showed that Triton X-114 could eliminate the residual endotoxin in the recombinant protein and had no effect on the immunogenicity of Fiber protein.

Example 18 Preparation and Immunogenicity Test of Five-Combined Vaccines of Newcastle Disease Virus, Avian Infectious Bronchitis Virus, Avian Influenza Virus, Egg Drop Syndrome Virus and Fowl Adenovirus 1. Preparation of Five-Combined Vaccine The fiber protein purified according to Example 17 was mixed with antigens of Newcastle disease virus prepared according to Example 10, avian influenza virus prepared according to Example 11, avian infectious bronchitis virus prepared according to Example 12, and fowl adenovirus prepared according to Example 14 in a certain ratio, respectively, and added to the white oil adjuvant, while the motor was started to stir the mixtures at 17500 r/min for 5 min. 1% thimerosal solution was added to a final concentration of 0.01% before termination of stirring. The component ratios are shown in Table 21.

TABLE 21

Component ratios of five-combined vaccine

| Component | Vaccine 20 |
|---|---|
| Antigen of N7a strain ($EID_{50}$/0.1 ml) | $10^{8.0}$ |
| Antigen of M41 strain ($EID_{50}$/0.1 ml) | $10^{6.0}$ |
| Antigen of SZ strain ($EID_{50}$/0.1 ml) | $10^{8.0}$ |
| Fiber protein (HA titer) | 1:32 |
| Fiber-2 protein (AGP titer) | 1:8 |
| White oil adjuvant (v/v %) | 66% |

2. Immunogenicity Test of Egg Drop Syndrome Virus Part of the Five-Combined Vaccine The immunogenicity of the egg drop syndrome virus part of the five-combined vaccine was verified with reference to the method in the immunogenicity test of egg drop syndrome virus part in Example 16 Part 1, group 85 was an immunization group and group 86 was a blank control. The results are shown in Table 22.

TABLE 22

Result of immunogenicity test of egg drop syndrome virus part of the five-combined vaccine

| | | | Results of determining HI antibody titers (log2) | |
|---|---|---|---|---|
| Group | Immune dose (ml per chicken) | Number of chickens | Before immunization | On the 21st day after immunization |
| 85 | 0.5 | 10 | 0 | 10.4 |
| 86 | 0.5 | 10 | 0 | 0 |

The results showed that, on Day 21 after immunization, the group immunized with vaccine 20 could produce a relatively higher HI antibody titer, and this effectively prevents occurrence of the egg drop syndrome in chickens. The results showed that the five-combined vaccine, in which the Fiber protein of egg drop syndrome virus was prepared as the antigen, could provide complete protection to chickens.

3. Immunogenicity Test of the Newcastle Disease Virus Part of the Five-Combined Vaccine The immunogenicity of the Newcastle disease virus part of the five-combined vaccine was verified with reference to the method in the immunogenicity test of Newcastle disease virus part in Example 16 Part 2, group 87 was an immunization group and group 88 was a blank control. The results are shown in Table 23.

TABLE 23

Results of immunogenicity test of the Newcastle disease
virus part of the five-combined vaccine

| | | | Results of determining HI antibody titer (log2) | | Results of challenge | | |
|---|---|---|---|---|---|---|---|
| Group | Immune dose (μl per chicken) | Number of chickens | Before immunization | Day 21 after immunization | Number of incidence | Number of deaths | Protection rate |
| 87 | 20 | 10 | 0 | 8.3 | 0/10 | 0/10 | 100% |
| 88 | 20 | 10 | 0 | 0 | 10/10 | 10/10 | 0 |

Note:
the HI antibody was determined as the geometric mean of the immunized chicken antibody.

The results showed that the group immunized with vaccine 20 could produce a relatively higher titer of Newcastle disease virus antibody, and compared with the control group, could provide complete protection against the virulent strain. The results showed that the combined vaccine, in which the Newcastle disease virus N7a strain solution was prepared as the antigen, could provide complete protection to chickens.

4. Immunogenicity Test of Avian Influenza Virus Part of the Five-Combined Vaccine The immunogenicity of the avian influenza virus part of the five-combined vaccine was verified with reference to the method in the immunogenicity test of avian influenza virus part in Example 16 Part 3, group 89 was an immunization group and group 90 was a blank control. The results are shown in Table 24.

TABLE 24

Results of immunogenicity test of the avian influenza virus
part of the five-combined vaccine

| | | | Results of determining HI antibody titer (log2) | | Results of challenge | |
|---|---|---|---|---|---|---|
| Group | Immune dose (ml per chicken) | Number of chickens | Before immunization | Day 21 after immunization | isolation rate of virus | Protection rate |
| 89 | 0.3 | 10 | 0 | 8.9 | 0/10 | 100% |
| 90 | 0.3 | 10 | 0 | 0 | 10/10 | 0 |

Note:
the HI antibody was determined as the geometric mean of the immunized chicken antibody.

The results showed that the group immunized with vaccine 20 could produce a higher titer of avian influenza virus antibody on Day 21 after immunization and compared with the control group, could provide complete protection against the virulent strain. The results showed that the five-combined vaccine, in which the H9 subtype of avian influenza virus solution was prepared as the antigen, could provide complete protection to chickens.

5. Immunogenicity Test of Avian Infectious Bronchitis Virus Part of the Five-Combined Vaccine The immunogenicity of the avian infectious bronchitis virus part of the five-combined vaccine was verified with reference to the method in the immunogenicity test of avian infectious bronchitis virus part in Example 16 Part 4, group 91 was an immunization group and group 92 was a blank control. The results are shown in Table 25.

TABLE 25

Results of immunogenicity test of avian infectious
bronchitis virus part of the five-combined vaccine

| Group | Antibody titers for the first immunization | Antibody titers for the second immunization | Factors of antibody titers for the first immunization versus antibody titers for the second immunization | isolation rate of virus after challenge |
|---|---|---|---|---|
| 91 | 1:20.4 | 1:123.2 | 6.0 | 0/10 |
| 92 | ≤1:4 | ≤1:4 | — | 5/5 |

The results showed that the geometric means of the HI antibody titers in the serums of second immunization for vaccine 20 were not less than 4 times of the geometric means of the HI antibody titers in the serums of first immunization, no virus was isolated from all of the tracheas of immunized chickens after challenge. The vaccine 20 could provide complete protection against the virulent strain. The results showed that the five-combined vaccine, in which the avian infectious bronchitis virus solution was prepared as the antigen, could provide complete protection to chickens.

6. Immunogenicity Test of the Fowl Adenovirus Part of the Five-Combined Vaccine

The immunogenicity of the fowl adenovirus part of the five-combined vaccine was verified with reference to the method in the immunogenicity test of fowl adenovirus part in Example 16 Part 6, group 93 was an immunization group and group 94 was a blank control. The results are shown in Table 26.

TABLE 26

Results of immunogenicity test of fowl adenovirus
part of the five-combined vaccine

| | Immune dose | | Results of challenge | | |
|---|---|---|---|---|---|
| Group | (ml per chicken) | Number of chickens | Number of incidence | Number of deaths | Protection rate |
| 93 | 0.3 | 10 | 0/10 | 0/10 | 100% |
| 94 | 0.3 | 10 | 10/10 | 10/10 | 0 |

The results showed that the immunization groups could produce better immune protection on Day 21 after immunization. The results showed that the five-combined vaccine, in which the fowl adenovirus Fiber-2 protein was prepared as the antigen, could provide complete protection to chickens.

The foregoing descriptions are merely preferred examples of the present disclosure and are not intended to limit the present disclosure in any form. Although the present disclosure has been disclosed by way of preferred examples, it is to be understood that the disclosure is not limited thereto. A person skilled in the art can make some equivalent variations or modifications to the above-disclosed technical content without departing from the scope of the technical solutions of the present disclosure to obtain equivalent examples. Simple modifications, equivalent changes and modifications made to the above examples according to the technical essence of the present disclosure all fall within the scope of the technical solutions of the present disclosure without departing from the contents of the technical solutions of the present disclosure.

The invention claimed is:

1. A vaccine composition against egg drop syndrome virus comprising an immune amount of antigen of egg drop syndrome virus and a veterinarily acceptable carrier, wherein the antigen of egg drop syndrome virus is an antigen of Fiber protein of egg drop syndrome virus or a live vector recombined with gene of the Fiber protein of egg drop syndrome virus, and the Fiber protein of egg drop syndrome virus is a protein encoded by a nucleotide sequence shown in SEQ ID NO:1 or SEQ ID NO:2.

2. The vaccine composition according to claim 1, wherein the Hemagglutination (HA) titer of the antigen of the Fiber protein of egg drop syndrome virus is equal to or greater than 1:32.

3. The vaccine composition according to claim 1, wherein the HA titer of the antigen of the Fiber protein of egg drop syndrome virus is between 1:32 and 1:128.

4. The vaccine composition according to claim 1, wherein the HA titer of the antigen of the Fiber protein of egg drop syndrome virus is between 1:32 and 1:64.

5. The vaccine composition according to claim 1, wherein the live vector recombined with the gene of the Fiber protein of egg drop syndrome virus is a recombinant attenuated *Salmonella*, a recombinant Newcastle disease virus, or a recombinant poxvirus.

6. The vaccine composition according to claim 1, wherein the veterinarily acceptable carrier comprises an adjuvant, which comprises one or more of (1) alumina gel adjuvant, saponins, Avridine, didecyl adipate (DDA); (2) water-in-oil emulsion, oil-in-water emulsion, water-in-oil-in-water emulsion; or (3) the polymers of acrylic or methaciylic acid, the copolymers of maleic anhydride and alkenyl derivative; and the Ribi adjuvant system, Block co-polymer, Syntex adjuvant formulation (SAF-m), monophosphoryl lipid A, lipid-amine adjuvant, heat-labile enterotoxin from *E. coli*, cholera toxin, muramyl dipeptide and Gel adjuvant.

7. The vaccine composition according to claim 6, wherein the adjuvant is a white oil adjuvant for preparation of water-in-oil emulsion.

8. The vaccine composition according to claim 6, wherein the concentration of the adjuvant ranges from 5% to 70% V/V.

9. The vaccine composition according to claim 8, wherein the concentration of the adjuvant ranges from 30% to 70% V/V.

10. The vaccine composition according to claim 9, wherein the concentration of the adjuvant is 66% V/V.

11. The vaccine composition according to claim 1, wherein the vaccine composition further comprises one or more antigens including an antigen of Newcastle disease virus, an antigen of avian influenza virus, an antigen of avian infectious bronchitis virus, an antigen of infectious bursal disease, an antigen of fowl adenovirus, an antigen of avian reovirus, an antigen of *Escherichia coli*, an antigen of *Avibacterium paragallinarum*, an antigen of *Mycoplasma Synoviae*, an antigen of *Mycoplasma gallisepticum*, an antigen of *Pasteurella multocida*, an antigen of Marek's disease virus, an antigen of avian encephalomyelitis virus and an antigen of infectious laryngotracheitis virus.

12. The vaccine composition according to claim 1, wherein the vaccine composition further comprises one or more antigens including an inactivated antigen of Newcastle disease virus, an inactivated antigen of avian influenza virus, an inactivated antigen of avian infectious bronchitis virus, a subunit antigen of infectious bursal disease virus, and an inactivated antigen or a subunit antigen of fowl adenovirus.

13. The vaccine composition according to claim 12, wherein the inactivated antigen of Newcastle disease virus is an inactivated antigen of N7a strain, the inactivated antigen of avian influenza virus are inactivated antigens of SZ strain, the inactivated antigen of avian infectious bronchitis virus are inactivated antigen of M41 strain, the subunit antigen of infectious bursal disease virus are VP2 protein of infectious bursal disease virus, the inactivated antigen of fowl adenovirus are inactivated antigens of FAV-HN strain, and the subunit antigen of fowl adenovirus are Penton protein or Fiber-2 protein of the fowl adenovirus.

14. The vaccine composition according to claim 12, wherein the HA titer of the Fiber protein of the egg drop syndrome virus is between 1:32 and 1:128, the content of the inactivated antigen of the Newcastle disease virus is $10^{8.0}$-$10^{9.0}$ $EID_{50}$/0.1 ml before inactivation, the content of the inactivated antigen of the avian influenza virus is $10^{6.5}$-$10^{8.5}$ $EID_{50}$/0.1 ml before inactivation, the content of the inactivated antigen of the avian infectious bronchitis virus is $10^{6.0}$-$10^{7.0}$ $EID_{50}$/0.1 ml before inactivation, and the agar gel precipitation (AGP) titer of the VP2 protein of the avian infectious bursal disease virus is between 1:16 and 1:128, the AGP titer of the Penton protein of the fowl adenovirus is between 1:2 and 1:16, and the AGP titer of the Fiber-2 protein of the fowl adenovirus is between 1:2 and 1:16.

15. The vaccine composition according to claim 14, wherein the HA titer of the Fiber protein of the egg drop syndrome virus is between 1:32 and 1:128, the content of the inactivated antigen of the Newcastle disease virus is $10^{80}$ $EID_{50}$/0.1 ml before inactivation, the content of the inactivated antigen of the avian influenza virus is $10^{8.0}$ $EID_{50}$/0.1 ml before inactivation, the content of the inactivated antigen of the avian infectious bronchitis virus is $10^{6.0}$ $EID_{50}$/0.1 ml before inactivation, and the AGP titer of the VP2 protein of the avian infectious bursal disease virus is 1:16, the AGP titer of the Penton protein of the fowl adenovirus is 1:4, and the AGP titer of the Fiber-2 protein of the fowl adenovirus is 1:4.

16. A preparation method of the vaccine composition according to claim 1, wherein the preparation method comprises:

step (1), cloning a gene of the Fiber protein of egg drop syndrome virus and recombining the gene of the Fiber protein of egg drop syndrome virus into an expression vector so as to obtain a recombinant expression vector recombined with the gene of the Fiber protein of egg drop syndrome virus;

step (2), transforming the recombinant expression vector recombined with the gene of the Fiber protein of egg drop syndrome virus and an expression vector of a molecular chaperone into *Escherichia coli* in order to express the Fiber protein of egg drop syndrome virus;

step (3), treating the expressed the Fiber protein of egg drop syndrome virus with a non-ionic surfactant in order to remove endotoxin; and step (4), mixing the Fiber protein of egg drop syndrome virus in which the endotoxin is removed with an adjuvant to obtain the vaccine composition.

17. A method of preventing and/or treating infection of egg drop syndrome virus by applying the vaccine composition according to claim 1.

* * * * *

SEQUENCE LISTING

<160> NUMBER OF SEQ ID NOS: 10

<210> SEQ ID NO 1
<211> LENGTH: 1560
<212> TYPE: DNA
<213> ORGANISM: Eggdrop syndrome-1976 virus

<400> SEQUENCE: 1

```
atgaaacgtc tgcgtctgga cccggacccg gtttacccgt tcggtacctc tgaaaccatc      60
ccgatgccgc cgttcatcga agctggttct ggtctggctg ttaacggtct gcagctgtac     120
atcaccgctc aggctccggt tggtttcacc aacaaagctg ttaccctgaa atacggtgac     180
ggtctggaag ttaacgaaaa cggtgaactg atcgctaccg cttcttctgc tgttaaaccg     240
ccgctgcact tcgaccgtgg ttacatcgtt ctgaacctgc aggacccgct gggtgttatc     300
gacggtaaac tgggtgttaa actgggtccg ggtgttcaca tcaacggtga aggtgctgtt     360
gctgttgaat ctccggttga cccgatcacc ctggacaccg ctggtcgtat caccctgaac     420
tacggtaccg gtctgaacgt ttctgacggt aaactgcgtc tggtttctcc ggaatctccg     480
ctgaccctgc tgggtaacgg taaagttgct ctgaacttcg gtaactctat ggaactggtt     540
cagggtaccc tgcagctgaa agctccgctg aacccgctgt tcatgacccc ggctggtgct     600
atcggtctgc gtgttgacga catgttcaac atctctgaag gtctgctgtc tttcaaaatg     660
ccgtctgacc cgatctcttt caacgctgac ggtatgctgt ctctgaacac caacgacacc     720
ctgcagacca ccggtggtct gctgggtctg accgaaccgg ctaaaccgct gaaactggct     780
gacggtaaac tgggtgttaa cgttggtctg ggtctggctg tttctaacgg ttctctgacc     840
gttaacgctg gtcagggtct gaccatccgt aacaacgctg ttgctgttaa cggtggtaac     900
accctggctt tcaacaacta cggtgaagtt gaactgaaaa acccgcgtaa cccgatcggt     960
ctgacccagg acggtgaact ggctctgatc atcggttacg gtctgaccac cctggacggt    1020
cgtctgaccc tgctgaccgc ttctacctct ccgatcgctg ttggtccgac cggtgttacc    1080
ttcaacgtta ccccgtctga cttctacttc ctgtcttcta aactggctct gaacgttgaa    1140
acccgtggtg gtctggaaaa atctgacacc ggtctgaaaa tcaaacgtgc tgctccgctg    1200
tctatcacct ctgacggtga actgaccctg gcttacgact ctaccgactt ccaggttacc    1260
gaaaacggtc tggctctgaa agtttctccg acccagaccc cgctgacccg tatcatctct    1320
atgggtaaca acctgttcga ctctggttac gaaatcttcg cttcttgccc gcagaacaaa    1380
gctgctaaag ttgctggtta cgtttacctg acctctgttg gtggtctggt tcacggtacc    1440
atccagatca aagctaccgc tggttactgg ttcaccggtg gtaactctgt tcaggaatct    1500
atccgtttcg gtctggttct gtgcccgttc tctgctcgtg acccgaccgc taacctgtct    1560
```

<210> SEQ ID NO 2
<211> LENGTH: 1947
<212> TYPE: DNA
<213> ORGANISM: Eggdrop syndrome-1976 virus

<400> SEQUENCE: 2

```
atgacaagac ccgcaaagcg actacggttg gaccctgatc ctgtttatcc cttcgggacg      60
agcgagacga tcccaatgcc tccgttcatc gaagctgggt caggtctagc agtaaatgga     120
ctgcagcttt atataacagc tcaagctccg gtgggcttca ccaacaaagc tgtaacatta     180
aaatatggag atggattgga agtaaatgaa aatggagaac tcatagctac ggcttcttcg     240
gcagtaaagc caccactcca ttttgatagg ggttatatag tgttaaatct tcaggatcca     300
```

```
ttgggtgtta ttgatgggaa gcttggggtc aagttaggcc ctggggttca catcaatggt       360 gaagggctg  tggcggtaga atccctgtg  accccatta  cacttgatac  ggctggtaga       420
attactttaa attatggcac aggtttaaat gtgagtgatg aaaattacg  actagtaagt       480 cctgaaagtc cgctcacact tcttggaaat ggcaaggttc tcttaatttt tggtaattca       540
atggagcttg tgcaagggac cttgcaactg aaagctccgc taaatccttt gttcatgacc       600
cccgcgggtg cgatcggctt aagggtggat gacatgttta acatttctga aggtttactc       660
tccttcaaga tgccatccga tccaatttcg tttaatgctg atggtatgtt gtctttgaac       720
acaaatgaca cattgcaaac aactggtggg ctgttagggt tgaccgaacc tgccaagccg       780
ttaaaattgg ccgatggcaa gttaggtgta atgtgggcc  ttgggttagc ggtttctaat       840
gggtcattga ctgtaaatgc agggcagggg ttgactattc gaataatgc  ggtggcagtt       900 aatgggggca acacgcttgc ttttaataat tatggagagg tggaacttaa aaaccctaga       960
aaccccataa gcctgaccca agatggtgaa ttggttttga taatcggtca tggcctaaca      1020
acccttgatg gacggctcac tctacttacc gcttcgacct ctccgatagc tgtagggcca      1080
accggtgtta catttaatgt tacaccgagt gatttttact ttttatctag taaattagct      1140
ctcaatgttg agaccccgtgg cggcttagaa aaagtgaca  ctggtttaaa aattaaacgt      1200 gcggccctc  tcagtatcac atctgatggt gagttgactt tggcttatga ttccacggat      1260
tttcaggtga cagaaaacgg cctagcccta aaggtatctc cgacgcagac ccctctcacc      1320
agaataattt ctatgggaaa taacttgttt gattctggtt atgagatttt tgcttcatgt      1380
ccgcagaaca aagcagcaaa ggttgcaggg tatgtgtatt aacatcggt  tggtgggctt      1440 gtacatggga ccattcagat taaagctact gcggggtatt ggtttacggg gggaaacagc      1500
gtgcaggaaa gtatcaggtt tggattggtg ttgtgtcctt ttagtgctcg cgacccact       1560 gctaacctgt caggctggcc agcgccagta gtgtggagtg gtgatagcaa tactcccta       1620 tattttgcgg ccaatgccat tagttatacc aataaccgtg taaatcttgc agttaccggt      1680
aacttttaca aggaggaaac cgaattgccg ggttacactc gtcattcttt ctgccctacc      1740
gggaccaccg gaatgaattt tacaggggt  aatttgtatg tgtgtccgtg cactgtaaat      1800 acagggcaa  ccacactgaa tgccatttat atggtgtttg tgattactca atcagctttg      1860
ggaactaatt tctttgcttc taacacccct cccaacacat tcttttaac  tcccccatt       1920 cccttacat  atgttggagc acagtag                                          1947
```

<210> SEQ ID NO 3
<211> LENGTH: 25
<212> TYPE: DNA
<213> ORGANISM: Artificial Sequence
<220> FEATURE:
<223> OTHER INFORMATION: Foward primer for amplification of gene of of
      Fiber protein of egg drop syndrome virus

<400> SEQUENCE: 3
atgaagcgac tacggttgga ccctg                                              25

<210> SEQ ID NO 4
<211> LENGTH: 25
<212> TYPE: DNA
<213> ORGANISM: Artificial Sequence
<220> FEATURE:
<223> OTHER INFORMATION: Reverse primer for amplification of gene of of
      Fiber protein of egg drop syndrome virus

```
<400> SEQUENCE: 4
ctactgtgct ccaacatatg taaag                                          25

<210> SEQ ID NO 5
<211> LENGTH: 32
<212> TYPE: DNA
<213> ORGANISM: Artificial Sequence
<220> FEATURE:
<223> OTHER INFORMATION: Foward primer for amplification of VP2 gene of
      infectious bursal disease virus

<400> SEQUENCE: 5
ccggaattca tgacaaacct gcaagatcaa ac                                  32

<210> SEQ ID NO 6
<211> LENGTH: 33
<212> TYPE: DNA
<213> ORGANISM: Artificial Sequence
<220> FEATURE:
<223> OTHER INFORMATION: Reverse primer for amplification of VP2 gene of
      infectious bursal disease virus

<400> SEQUENCE: 6
acgcgtcgac ttaccttagg gcccggatta tgt                                 33

<210> SEQ ID NO 7
<211> LENGTH: 17
<212> TYPE: DNA
<213> ORGANISM: Artificial Sequence
<220> FEATURE:
<223> OTHER INFORMATION: Foward primer for amplification of gene of
      Fiber-2 protein of fowl adenovirus

<400> SEQUENCE: 7
ctccgggccc ctaaaag                                                   17

<210> SEQ ID NO 8
<211> LENGTH: 15
<212> TYPE: DNA
<213> ORGANISM: Artificial Sequence
<220> FEATURE:
<223> OTHER INFORMATION: Reverse primer for amplification of gene of
      Fiber-2 protein of fowl adenovirus

<400> SEQUENCE: 8
cgggacggag gccgc                                                     15

<210> SEQ ID NO 9
<211> LENGTH: 48
<212> TYPE: DNA
<213> ORGANISM: Artificial Sequence
<220> FEATURE:
<223> OTHER INFORMATION: Foward primer for amplification of gene of
      Fiber protein of egg drop syndrome virus

<400> SEQUENCE: 9
catgccatgg gcatgacaag acccgcaaag cgactacggt tggaccct                 48

<210> SEQ ID NO 10
<211> LENGTH: 29
<212> TYPE: DNA
<213> ORGANISM: Artificial Sequence
```

-continued

```
<220> FEATURE:
<223> OTHER INFORMATION: Reverse primer for amplification of gene of
      Fiber protein of egg drop syndrome virus

<400> SEQUENCE: 10
ccgctcgagc tactgtgctc caacatatg                                  29
```